US009844504B2

(12) United States Patent
Villanueva et al.

(10) Patent No.: US 9,844,504 B2
(45) Date of Patent: Dec. 19, 2017

(54) CUSTOM DESIGNED MICROBUBBLE CONTRAST AGENTS AND TECHNIQUES OF ULTRASOUND DELIVERY OPTIMIZED FOR GENE THERAPY

(75) Inventors: Flordeliza Villanueva, Pittsburgh, PA (US); Andrew Carson, New Castle, PA (US); Charles F. McTiernan, Pittsburgh, PA (US); Jianjun Wang, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 775 days.

(21) Appl. No.: 13/640,954

(22) PCT Filed: Apr. 15, 2011

(86) PCT No.: PCT/US2011/032725
§ 371 (c)(1),
(2), (4) Date: Nov. 16, 2012

(87) PCT Pub. No.: WO2011/130658
PCT Pub. Date: Oct. 20, 2011

(65) Prior Publication Data
US 2013/0204166 A1 Aug. 8, 2013

Related U.S. Application Data
(60) Provisional application No. 61/426,782, filed on Dec. 23, 2010, provisional application No. 61/325,060, filed on Apr. 16, 2010.

(51) Int. Cl.
| | |
|---|---|
| *A61K 9/00* | (2006.01) |
| *A61N 7/00* | (2006.01) |
| *B65D 25/00* | (2006.01) |
| *A61K 41/00* | (2006.01) |
| *C12N 15/11* | (2006.01) |
| *A61K 48/00* | (2006.01) |
| *C12N 15/113* | (2010.01) |

(52) U.S. Cl.
CPC .......... *A61K 9/0002* (2013.01); *A61K 9/0009* (2013.01); *A61K 41/0028* (2013.01); *A61K 48/0083* (2013.01); *A61N 7/00* (2013.01); *B65D 25/00* (2013.01); *C12N 15/111* (2013.01); *A61N 2007/0039* (2013.01); *C12N 15/1138* (2013.01); *C12N 2310/14* (2013.01); *C12N 2320/32* (2013.01)

(58) Field of Classification Search
None
See application file for complete search history.

(56) References Cited

FOREIGN PATENT DOCUMENTS

| WO | WO 2005/063305 | 7/2005 |
| WO | WO 2009/035804 | 3/2009 |

OTHER PUBLICATIONS

Suzuki, et al. (Mar. 3, 2010; available Oct. 31, 2009 online) "Cancer gene therapy by IL-12 gene delivery using liposomal bubbles and tumoral ultrasound exposure", Journal of Controlled Release, 142(2): 245-50.*
Suzuki, et al. (2003) "Ultrasound-Microbubble-Mediated Intercellular Adhesion Molecule-1 Small Interfering Ribonucleic Acid Transfection Attenuates Neointimal Formation After Arterial Injury in Mice", Journal of the American College of Cardiology, 55(9): 904-13.*
Aoi, et al. (2008) "Herpes Simplex Virus Thymidine Kinase-Mediated Suicide Gene Therapy Using Nano/Microbubbles and Ultrasound", Ultrasound in Medicine & Biology, 34(3): 425-34.*
Hoffman and Wildner (Aug. 3, 2006) "Efficient generation of double heterologous promoter controlled oncolytic adenovirus vectors by a single homologous recombination step in *Escherichia coli*", BMC Biotechnology, 6(36): 1-12 (digital copy).*
Zhang, et al. (2011) "Preclinical Lymphatic Imaging", Molecular Imaging in Biology, 13(4): 599-612, downloaded asNIH Public Access document, 26 pages long.*
Heo (2002) "Progress and limitations in cancer gene therapy", Genetics in Medicine, 4(6 Suppl): 52S-55S.*
Hermanek (1999) "Disseminated tumor cells versus micrometastasis: definitions and problems", Anticancer Research, 19(4A): 2771-74 (Abstract Only).*
Akimoto, et al.,"Growth Inhibition of Cultured Human Tenon's Fibroblastic Cells by Targeting the E2F Transcription Factor." Exp. Eye Res., 67:395-401 (1998).
Aoi, et al., "Herpes Simplex Virus Thymidine Kinase-Mediated Suicide Gene Therapy Using Nano/Microbubbles and Ultrasound." Ultrasound Med Biol., 34:425-434 (2008).

(Continued)

*Primary Examiner* — Robert M Kelly
(74) *Attorney, Agent, or Firm* — Medlen & Carroll, LLP

(57) ABSTRACT

The invention pertains to a lipid-based microbubble stably binding a plurality of nucleic acids, and a method of delivering the microbubble and nucleic acids to a specific target site using ultrasound. The delivered nucleic acids create transgenic cells (i.e., for example, a transgenic tumor cell), wherein the transgenic cell expresses the proteins encoded by the delivered nucleic acids. This technology provides a significant improvement for microbubble-drug delivery platforms as known microbubble do not efficiently bind nucleic acids. The improvements described herein include but are not limited to identifying proper lipid proportionality ratios and/or cationic surfactant layers that provide an optimum mechanical index compatible with ultrasonics. Microbubble perfusion and/or nucleic acid delivery may be performed by a combination of imaging and ultrasound/microbubble targeted delivery to simultaneously perform low power two-dimensional imaging and high power microbubble destruction. Such systems are useful in therapeutics and/or diagnostics. For example, the data disclosed herein shows proof of principle in conjunction with the delivery of therapeutic siRNA molecules to slow tumor growth.

12 Claims, 23 Drawing Sheets

(56) References Cited

OTHER PUBLICATIONS

Bekeredjian, et al., "Ultrasound-Targeted Microbubble Destruction Can Repeatedly Direct Highly Specific Plasmid Expression to the Heart." Circulation, 108:1022-1026 (2003).

Berkowitz, et al., "The X-ray Crystal Structure of the NF-kB p50•p65 Heterodimer Bound to the Interferon β-kB site." J. Biol. Chem., 277:24694-24700 (2002).

Bhattacharya, et al., "Tumor Vascular Maturation and Improved Drug Delivery Induced by Methylselenocysteine Leads to Therapeutic Synergy With Anticancer Drugs." Clin Cancer Res., 14:3926-3932 (2008).

Boccaccio, et al., "Induction of Epithelial Tubules by Growth Factor HGF Depends on the STAT Pathway." Nature, 391:285-288(1998).

Bonner, et al., "Radiotherapy plus cetuximab for squamous-cell carcinoma of the head and neck." N Engl J Med., 354:567-78 (2006).

Bowman, et al., "STATs in Oncogenesis." Oncogene, 19:2474-2488 (2000).

Bowman, et al., "Stat3-Mediated Myc Expression Is Required for Src Transformation and PDGF-Induced Mitogenesis." Proc. Natl. Acad. Sci., USA, 98:7319-7324 (2000).

Bromberg, et al., "Stat3 As an Oncogene." Cell, 98:295-303 (1999).

Bromberg & Darnell, Jr., The Role of STATs in Transcriptional Control and Their Impact on Cellular Function. Oncogene, 19:2468-2473 (2000).

Catlett-Falcone, et al.,"STAT Proteins As Novel Targets for Cancer Therapy. Signal Transducer an Activator of Transcription." Curr. Opin. Oncol., 11:490-96 (1999).

Carson, et al., "Gene Therapy of Carcinoma Using Ultrasound-Targeted Microbubble Destruction." Ultrasound Med Biol., 37(3):393-402 (2011).

Chappell and Price, " Targeted Therapeutic Applications of Acoustically Active Microspheres in the Microcirculation." Microcirculation, 13:57-70 (2006).

Chen, et al., "Efficient Gene Delivery to Pancreatic Islets With Ultrasonic Microbubble Destruction Technology." PNAS, 103:8469-8474 (2006).

Chen, et al., "Reversal of Streptozotocin Induced Diabetes in Rats by Gene Therapy With Betacellulin and Pancreatic Duodenal Homeobox-1." Gene Therapy, 14:1102 (2007).

Chen, et al., "Enhancement of Survivin Gene Downregulation and Cell Apoptosis by a Novel Combination: Liposome Microbubbles and Ultrasound Exposure." Med Oncol., 26:491-500 (2009a).

Chen, et al., "Induced Apoptosis With Ultrasound Mediated Microbubble Destruction and shRNA Targeting Survivin in Transplanted Tumors." Adv Ther ., 26:99-106 (2009b).

Chen, et al., "Regeneration of pancreatic islets in vivo by ultrasound-targeted gene therapy." Gene Ther., 17(11):1411-20 (2010).

Christiansen, et al., "Targeted Tissue Transfection With Ultrasound Destruction of Plasmid-Bearing Cationic Microbubbles." Ultrasound Med Biol., 29:1759-1767 (2003).

Crinelli, et al., "Design and Characterization of Decoy Oligonucleotides Containing Locked Nucleic Acids." Nucleic Acids Res., 30:2435-2443 (2002).

Cross, et al., "Gene therapy for cancer treatment: Past, present and future." Clin Med Res., 4:218-227 (2006).

Darnell, "STATs and Gene Regulation." Science, 277:1630-1635 (1997).

deJong, et al., "Basic Acoustic Properties of Microbubbles." Echocardiography, 19:229-240 (2002).

Escalante, et al., "Structure of the NF-kB p50/p65 Heterodimer Bound to the PRDII DNA Element From the Interferon-β Promoter." Structure, 10:383-391 (2002).

Fry, et al., "A specific inhibitor of the epidermal growth factor receptor tyrosine kinase." Science, 265:1093- 1095 (1994).

Fu, et al., "Modification of the Effects of Continuous Low Dose Rate Irradiation by Concurrent Chemotherapy Infusion." Int J Radiat Oncol Biol Phys., 10:1473-1478 (1984).

Fujii, et al., "Ultrasound-Targeted Gene Delivery Induces Angiogenesis After a Myocardial Infarction in Mice." J Am Coll Cardiol Cardiovasc Imaging, 2:869-879 (2009).

Gambari, et al., "Decoy Oligodeoxyribonucleotides and Peptide Nucleic Acids—DNA Chimeras Targeting Nuclear Factor Kappa-B: Inhibition of IL-8 Gene Expression in Cystic Fibrosis Cells Infected With *Pseudomonas aeruginosa*." Biochem Pharmacol., 80(12):1887-1894 (2010).

Garcia, et al., "Constitutive Activation of Stat3 by the Src and JAK Tyrosine Kinases Participates in Growth Regulation of Human Breast Carcinoma Cells." Oncogene, 20:2499-2513 (2001).

Gavrieli, et al., "Identification of Programmed Cell Death in Situ Via Specific Labeling of Nuclear DNA Fragmentation." J Cell Bio., 19:493-501(1992).

Gomori, "A Rapid One-Step Trichrome Stain." Am J Clin Pathol., 20:661-663 (1950).

Gouilleux-Gruart, et al., "STAT-related transcription factors are constitutively activated in peripheral blood cells from acute leukemia patients." Blood, 87:1692-1697 (1996).

Grandis, et al., "Requirement of Stat3 but not Stat1 Activation for Epidermal Growth Factor Receptor—mediated Cell Growth in Vitro." J. Clin. Invest., 102:1385-1392 (1998a).

Grandis, et al., "Levels of TGF-α and EGFR Protein in Head and Neck Squamous Cell Carcinoma and Patient Survival." J. Natl. Cancer Inst., 90:824-832 (1998b).

Grandis, et al., "Epidermal Growth Factor Receptor—Mediated Stat3 Signaling Blocks Apoptosis in Head and Neck Cancer." Laryngoscope, 110;868-874 (2000).

Grandis, et al., "Constitutive Activation of Stat3 Signaling Abrogates Apoptosis in Squamous Cell Carcinogenesis in Vivo." Proc. Natl. Acad. Sci., USA, 97:4227-4232 (2000).

Greco, et al., "Eradication of Therapy-resistant Human Prostate Tumors Using an Ultrasound-guided Site-specific Cancer Terminator Virus Delivery Approach." Molecular Therapy, 18:295-306(2010).

Hayashi, et al., "Effect of Sonoporation on Cationic Liposome-Mediated Ifnbeta Gene Therapy for Metastatic Hepatic Tumors of Murine Colon Cancer." Cancer Gene Ther., 16:638-643(2009).

Hershberger, et al., "Calcitriol (1,25-Dihydroxycholecalciferol) Enhances Paclitaxel Antitumor Activity In Vitro and In Vivo and Accelerates Paclitaxel-Induced Apoptosis." Clin Cancer Res., 7:1043-1051 (2001).

Huang, et al., "Constitutive Activation of Stat 3 Oncogene Product in Human Ovarian Carcinoma Cells." Gynecol Oncol., 79:67-73 (2000).

Jayaweera, et al., "In-Vivo Myocardial Kinetics of Air-Filled Albumin Microbubbles During Myocardial Contrast Echocardiography: Comparison With Radiolabeled Red Blood Cells." Circ Res., 74:1157-1165 (1994).

Karin, "Too Many Transcription Factors: Positive and Negative Interactions." New Biol., 2(2):126-131 (1990).

Kaul, "Myocardial Contrast Echocardiography. A 25 Year Perspective." Circulation, 118:291-308 (2008).

Kijima, et al., "STAT3 Activation Abrogates Growth Factor Dependence and Contributes to Head and Neck Squamous Cell Carcinoma Tumor Growth in Vivo" Cell Growth Differ., 13:355-362 (2002).

Kirby, et al., "Gefitinib (ZD1839, Iressa) as palliative treatment in recurrent or metastatic head and neck cancer." Br J Cancer, 94:631-6 (2006).

Lai, et al., "Intratumoral epidermal growth factor receptor antisense DNA therapy in head and neck cancer: first human application and potential antitumor mechanisms." J Clin Oncol., 27(8):1235-42 (2009).

Latchman, "Transcription Factors: An Overview." Int. J. Biochem., Cell Biol. 29(12):1305-1312 (1997).

Lee, et al., "Transcription of Eukaryotic Protein-Coding Genes." Annu. Rev. Genet., 34:77-137 (2000).

Leong, et al., "Targeted inhibition of Stat3 with a decoy oligonucleotide abrogates head and neck cancer cell growth," PNAS, 100(7):4138-1143 (2003).

Li, et al., "IKKα, IKKβ and NEMO/IKKγ Are Each Required for the NF-Kb Mediated Inflammatory Response Program." J. Biol. Chem., 277:17397-17405 (2002).

(56) References Cited

OTHER PUBLICATIONS

Li, et al., "Optimising Ultrasound-Mediated Gene Transfer(Sonoporation) in Vitro and Prolonged Expression of a Transgene in Vivo: Potential Applications for Gene Therapy of Cancer." Cancer Lett., 273:62-69 (2009).
Libermann, et al., "Targeting Transcription Factors for Cancer Gene Therapy." Curr Gene Ther., 6(1):17-33 (2006).
Maeda, et al., "Targeted Drug Delivery System for Oral Cancer Therapy Using Sonoporation." J Oral Pathol Med., 38:572-579 (2009).
Matsuda, et al., "Nuclear Factor-kappaB Decoy Oligodeoxynucleotides Prevent Acute Lung Injury in Mice With Cecal Ligation and Puncture-Induced Sepsis." Mol Pharmacol., 67:1018-1025 (2005).
Meijering, et al., "Ultrasound and Microbubble-Targeted Delivery of Macromolecules Is Regulated by Induction of Endocytosis and Pore Formation." Circ Res., 104:679-687(2009).
Mitchell, et al., "Transcriptional regulation in mammalian cells by sequence-specific DNA binding proteins." Science, 245(4916): 371-378 (1989).
Morishita, et al., "In Vivo Transfection of Cis Element "Decoy" Against Nuclear Factor-Kβ Binding Site Prevents Myocardial Infarction." Nature (Lond) Med., 8:894-899 (1997).
Nabel, et al., "Site-Specific Gene Expression in Vivo by Direct Gene Transfer Into the Arterial Wall." Science, 249:1285-1288 (1990).
Nakajima, et al., "A central role for Stat3 in IL-6-induced regulation of growth and differentiation in M1 leukemia cells." EMBO J., 15:3651-3658 (1996).
Nayak and Herzog, "Progress and Prospects: Immune Responses to Viral Vectors." Gene Ther., 17:295-304 (2010).
Nie, et al., "Anti-Angiogenic Gene Therapy for Hepatocellular Carcinoma Mediated by Microbubble-Enhanced Ultrasound Exposure: an in Vivo Experimental Study." J Drag Target, 16:389-395 (2008).
Nielsen, et al., "Solution Structure of an LNA hybridized to DNA: NMR Study of the d(CTLGCTLTLCTLGC) : d(GC AG A AGC AG) Duplex Containing Four Locked Nucleotides." Bioconjugate Chem., 11:228-238 (2000).
Nikolov, et al., "RNA Polymerase II Transcription Initiation: A Structural View." Proc. Natl. Acad. Sci. U.S.A., 94(1):15-22 (1997).
Niu, et al.,"Constitutive Stat3 activity up-regulates VEGF expression and tumor angiogenesis." Oncogene, 21:2000-2008 (2002).
Park, et al., "Dual blockade of cyclic AMP response element—(CRE) and AP-1-directed transcription by CRE-transcription factor decoy oligonucleotide. gene-specific inhibition of tumor growth." J. Biol. Chem., 274:1573-1580 (1999).
Parryl, et al., "PET Imaging of Heat-Inducible Suicide Gene Expression in Mice Bearing Head and Neck Squamous Cell Carcinoma Xenografts." Cancer Gene Therapy, 16:161-170 (2009).
Petersen, et al., "The Conformations of Locked Nucleic Acids (LNA)." J. Mol. Recognit., 13:44-53 (2000).
Price, et al., "Delivery of Colloidal Particles and Red Blood Cells to Tissue Through Micro Vessel Ruptures Created by Targeted Microbubble Destruction With Ultrasound." Circulation, 98:1264-1267 (1998).
Ptashne, et al., "Transcriptional Activation by Recruitment." Nature, 386(6625):569-577 (1997).
Rainov, "A Phase III Clinical Evaluation of Herpes Simplex Virus Type 1 Thymidine Kinase and Ganciclovir Gene Therapy As an Adjuvant to Surgical Resection and Radiation in Adults With Previously Untreated Glioblastoma Multiforme." Hum Gene Ther., 11:2389-2401 (2000).
Reinhold and Visser, "In Vivo Fluorescence of Endothelial Cell Nuclei Stained With the Bis-Benzamide H33342." Int J Microcirc Clin Exp., 2:143-146 (1983).
Roeder, "The Role of General Initiation Factors in Transcription by RNA Polymerase II." Trends Biochem. Sci., 21(9):327-335 (1996).
Sadowski, et al., "A Common Nuclear Signal Transduction Pathway Activated by Growth Factor and Cytokine Receptors." Science, 261:1739-1744 (1993).
Sambrook, et al., In: Molecular Cloning: A Laboratory Manual, Cold Spring Harbor Press, NY, pp. 7.39-7.52 (1989).
Sambrook, et al., In: Molecular Cloning: A Laboratory Manual, Cold Spring Harbor Press, NY, pp. 9.31-9.58 (1989).
Sawa, et al., "A Novel Strategy for Myocardial Protection Using in Vivo Transfection of Cis Element 'Decoy' Against NFkappaB Binding Site: Evidence for a Role of NFkappaB in Ischemia-Reperfusion Injury." Circulation, 96(Suppl. 9):5280-5284 (1997).
Sen, et al.," Lack of Toxicity of a STAT3 Decoy Oligonucleotide." Cancer Chemother Pharmacol., 63:983-995 (2009).
Shand, et al., "A Phase 1-2 Clinical Trial of Gene Therapy for Recurrent Glioblastoma Multiforme by Tumor Transduction With the Herpes Simplex Thymidine Kinase Gene Followed by Ganciclovir." Hum Gene Ther., 10:2325-2335 (1999).
Sharma, et al., "Transcription Factor Decoy Approach to Decipher the Role of NF-kappa B in Oncogenesis." Anticancer Res., 16:61-69 (1996a).
Sharma , et al., "The NF-kappaB Transcription Factor in Oncogenesis." Anticancer Res., 16:589-596 (1996b).
Shen, et al., "Constitutively Activated Stat3 Protects Fibroblasts From Serum Withdrawal and UV-Induced Apoptosis and Antagonizes the Proapoptotic Effects of Activated Stat1." Proc. Natl. Acad. Sci. USA, 98:1543-1548 (2001).
Shen, et al., "DNA Diffusion in Mucus: Effect of Size, Topology of DNAs, and Transfection Reagents." Biophys J., 91:639-644 (2006).
Thomas and Grandis, "The Current State of Head and Neck Cancer Gene Therapy." Hum Gene Ther., 8:2110-2120 (2009).
Timchenko, et al., "Modified DNA Fragments Specifically and Irreversibly Bind Transcription Factor NF-KappaB in Lysates of Human Tumor Cells." Biochemistry (Mosc), 71(4):454-460 (2006).
Turkson, et al., "Requirement for Ras/Racl-Mediated P38 and C-Jun N-Terminal Kinase Signaling in Stat3 Transcriptional Activity Induced by the Src Oncoprotein." Mol. Cell. Biol., 19:7519-7528 (1999).
Turkson, et al., "Phosphotyrosyl Peptides Block Stat3-Mediated DNA Binding Activity, Gene Regulation, and Cell Transformation." J. Biol. Chem., 276:45443-45455 (2001).
van Wamel, et al., "Micromanipulation of Endothelial Cells:Ultrasound-Microbubble-Cell Interaction." Ultrasound Med Biol., 30:1255-1258 (2004).
Villanueva and Wagner, "Ultrasound Molecular Imaging of Cardiovascular Disease." Nature Clin Prac Cardiovasc Med., 5:26-32 (2008).
Villanueva, "Ultrasound Mediated Destruction of DNA-Loaded Microbubbles for Enhancement of Cell-Based Therapies: New Promise Amidst a Confluence of Uncertainties?" J Am Coll Cardiol Imaging, 2:880-882 (2009).
Wagner, et al.,"The SIF Binding Element Confers sis/PDGF Inducibility Onto the c-fos Promoter." EMBO J., 9:4477-4484 (1990).
Wang, et al., "Targeted Disruption of Stat6 DNA Binding Activity by an Oligonucleotide Decoy Blocks IL-4 Driven TH2 Cell Response." Blood, 95:1249-1257 (2000).
Weller, et al., "Modulating Targeted Adhesion of an Ultrasound Contrast Agent to Dysfunctional Endothelium." Ann Biomed Eng., 30:1012-1019 (2002).
Weller, et al., "Ultrasonic Imaging of Tumor Angiogenesis Using Contrast Microbubbles Targeted Via the Tumor-Binding Peptide RRL." Cancer Res., 65:533-539 (2005).
Whitehead, et al., "Knocking Down Barriers: Advances in siRNA Delivery." Nature Reviews Drug Discovery, 8: 129-138 (2009).
Whitehead, et al., "Knocking Down Barriers: Advances in siRNA Delivery." Nature Reviews Drug Discovery, 8:129-138 erratum (2009).
Xi, et al., "In Vivo Antitumor Efficacy of STAT3 Blockade Using a Transcription Factor Decoy Approach: Implications for Cancer Therapy." Oncogene, 24:970-979 (2005).
Yu, et al., "Enhanced DNA-Binding Activity of a Stat3-Related Protein in Cells Transformed by the Src Oncoprotein." Science, 269:81-83 (1995).
Zhang, et al., "Intravenous RNA Interference Gene Therapy Targeting the Human Epidermal Growth Factor Receptor Prolongs Survival in Intracranial Brain Cancer." Clin Cancer Res., 10:3667-3677 (2004).

(56) References Cited

OTHER PUBLICATIONS

Zhao, et al., "Asymmetric Oscillation of Adherent Targeted Ultrasoundcontrast Agents." Appl Phys Lett., 87:134103-134106 (2005).
International Search Report (ISR) PCT/US2011/032725.
Hernot and Klibanov, "Microbubbles in Ultrasound-Triggered Drug and Gene Delivery." Adv Drug Deliv Rev., 60(10): 1153-1166 (2008).
Kinoshita and Hynynen, "A Novel Method for the Intracellular Delivery of Sirna Using Microbubble-Enhanced Focused Ultrasound. " Biochem Biophys Res Commun., 335(2):393-9 (2005).
Lentacker, et al., "Ultrasound Exposure of Lipoplex Loaded Microbubbles Facilitates Direct Cytoplasmic Entry of the Lipoplexes." Mol Pharm., 6(2):457-67 (2009).
Negishi, et al., "Delivery of siRNA Into the Cytoplasm by Liposomal Bubbles and Ultrasound." J Control Release, 132(2):124-30 (2008).
Schlee, et al., "siRNA and isRNA: Two Edges of One Sword." Mol Ther., 14(4):463-70 (2006).

\* cited by examiner

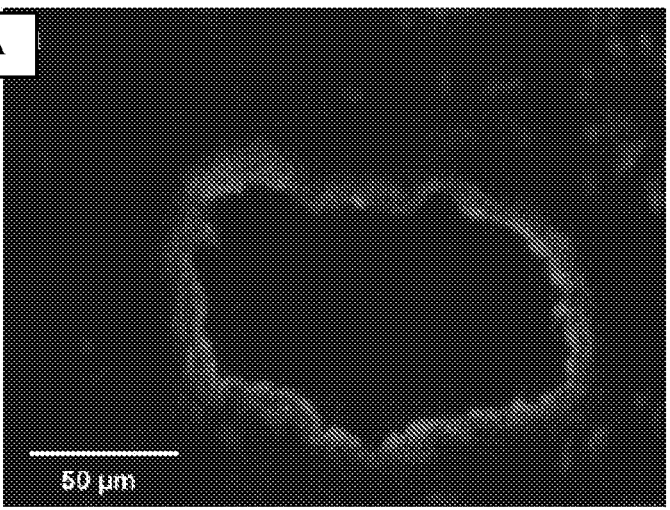
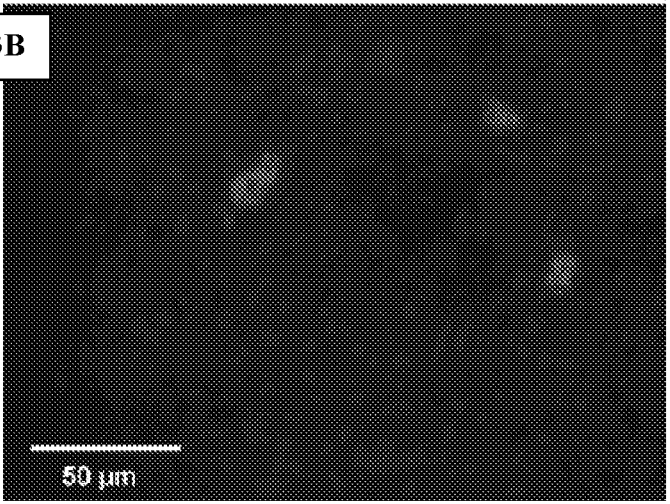
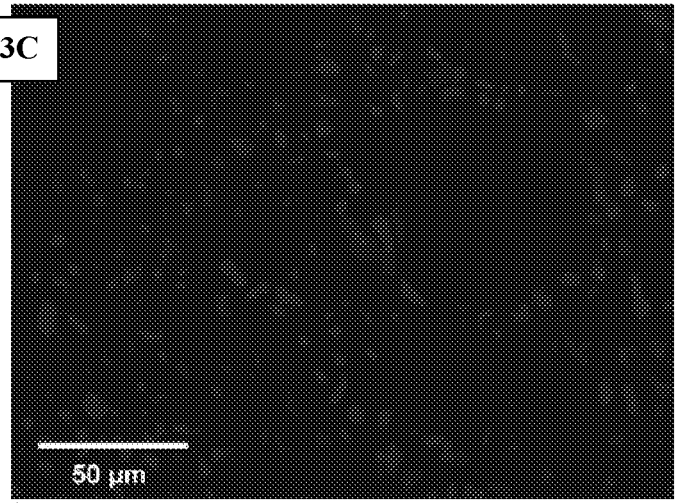

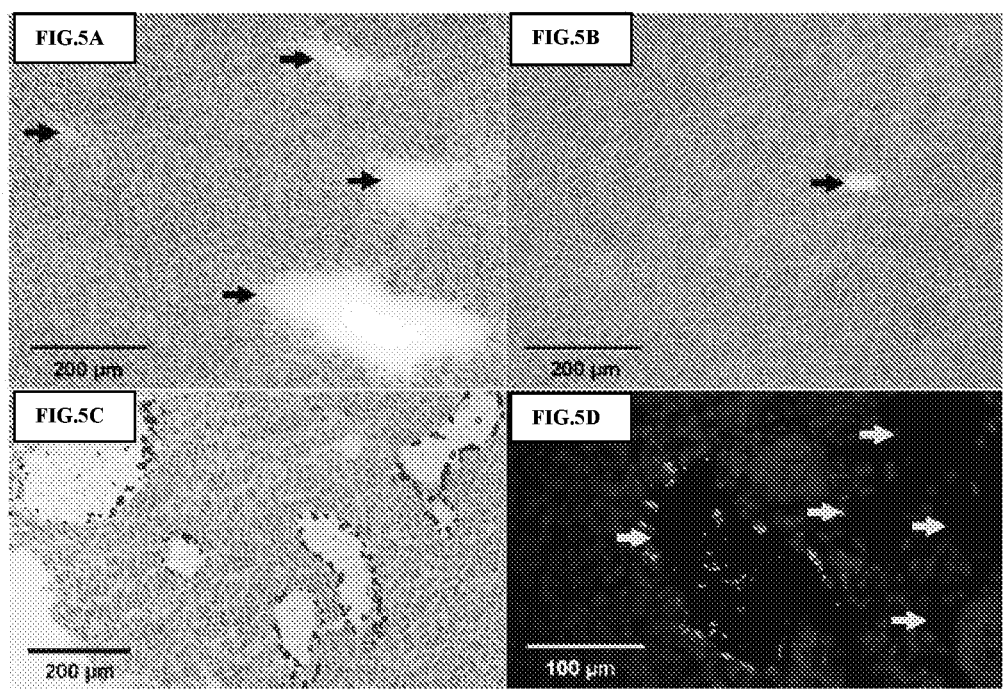

CUSTOM DESIGNED MICROBUBBLE CONTRAST AGENTS AND TECHNIQUES OF ULTRASOUND DELIVERY OPTIMIZED FOR GENE THERAPY

This application for patent under 35 U.S.C. §371(F) claims benefit of priority, to PCT Application Serial Number PCT7US11/32725, filed on 04/15/2011, now abandoned, and to U.S. Provisional Application Serial Number 61/426.782, filed on 12/23/2010, now abandoned, and to U.S. Provisional Application Serial Number 61/325.060, filed on 04/16/2010, now abandoned, under 35 U.S.C. §111(b), the disclosures of each of which are herein incorporated bv reference in its entirety.

FIELD OF INVENTION

This invention is related to the field of gene and molecular therapeutics. Some embodiments of the present invention provide Ultrasound/Microbubble Targeted Delivery (UMTD) of genes that slow tumor growth. For example, in a mouse model of squamous cell carcinoma (SCC-VII) UMTDs delivered a Herpes Simplex Virus type 1 Thymidine Kinase (TK) gene to tumors as a suicide gene. Other medical conditions may be treated with UMTD by deliverying oligonucleotide therapeutic molecules (e.g., transcription factor decoy molecules).

BACKGROUND

Ultrasound/Microbubble Targeted Delivery (UMTD) has great potential to treat solid tumors UMTD has delivered both reporter and therapeutic genes to a variety of tissues in vivo UMTD has delivered genes to tumors, but only if Microbubbles (MBs) were injected directly into the tumor prior to Ultrasound (US) treatment Several genes (such as HSV-TK) have shown to be effective at reducing the growth of tumors in other gene therapy studies.

Although there is great potential for this system, there are several limitations that need overcome—MBs used for gene therapy are not optimized for DNA binding—US delivery conditions must allow for full perfusion of the target tissue prior to destruction and insonify MBs way that transduces target tissue—Mechanism of UMTD mediated gene therapy is not entirely understood and efficiency is rather low.

The use of UMTD has several important advantages— MBs are a nonviral delivery platform that can be used repeatedly, and are likely to be safe—US can spatially target expression of the transgene—MBs can load genes, RNA, oligos, drugs, or a mix, making this a very flexible delivery platform

SUMMARY

This invention is related to the field of gene and molecular therapeutics. Some embodiments of the present invention provide ultrasound/microbubble targeted delivery (UMTD) of genes that slow tumor growth. For example, in a mouse model of squamous cell carcinoma (SCC-VII) UMTDs delivered a Herpes Simplex Virus type 1 Thymidine Kinase (TK) gene to tumors as a suicide gene. Other medical conditions may be treated with UMTD by delivering oligonucleotide therapeutic molecules (e.g., transcription factor decoy molecules).

In one embodiment, the present invention contemplates a composition comprising an ultrasound targeted microbubble population, wherein the microbubble population stably binds a plurality of nucleic acids. In one embodiment, the nucleic acids are selected from the group including but not limited to oligonucleotide therapeutic molecules, siRNA, shRNA, RNAi, miRNA, antisense, transcription factor decoy molecules, deoxyribonucleic acid vectors, genes, and/or gene fragments. In one embodiment, the siRNA is an EGFR siRNA. In one embodiment, the transcription factor decoy molecule is an NF-kB transcription factor decoy molecule. In one embodiment, the transcription factor decoy molecule is a STAT 3 transcription factor decoy molecule. In one embodiment, the deoxyribonucleic acid vector comprises a cytomegalovirus promoter sequence and a herpes simplex virus thymidine kinase sequence (pCMV-TK). In one embodiment, the microbubble population comprises a positively charged lipid shell. In one embodiment, the stably bound nucleic acids are deoxyribonuclease-resistant. In one embodiment, the stably bound nucleic acids are ribonuclease-resistant. In one embodiment, the stably bound nucleic acids are resistant to repetitive washings. In one embodiment, the microbubble population comprises a mixture of 1,2-distearoyl-sn-glycero-3-ethylphosphocholine (DSEPC), distearoylphosphatidyl-choline (DSPC), and PEG-40. In one embodiment, the mixture is a 7:14:1 mixture. In one embodiment, the microbubble population comprises a mechanical index of approximately 1.6. In one embodiment, the microbubble population comprises a bursting threshold at approximately 1.3 MHz.

In one embodiment, the present invention contemplates a method for creating a transgenic target cell, comprising: a) providing; i) a plurality of target cells; ii) an ultrasound targeted microbubble population stably binding a plurality of nucleic acids; iii) an ultrasound device capable of directing said microbubble population to said target cells; and b) directing said microbubble population to said target cells with said first ultrasound device; c) bursting said microbubble population under conditions such that a transgenic target cell is created. In one embodiment, the ultrasound device bursts said microbubble population at approximately 1.3-1.4 MHz. In one embodiment, the plurality of target cells is a cell culture. In one embodiment, the plurality of target cells is a bodily tissue. In one embodiment, the bodily tissue is a tumor. In one embodiment, the cell culture is a cancer cell culture. In one embodiment, the tumor comprises colorectal cancer cells. In one embodiment, the tumor comprises squamous cell carcinoma cells. In one embodiment, the transgenic target cell expresses said plurality of nucleic acids. In one embodiment, the nucleic acids are selected from the group including but not limited to oligonucleotide therapeutic molecules, siRNA, shRNA, RNAi, miRNA, antisense, transcription factor decoy molecules, deoxyribonucleic acid vectors, genes, and/or gene fragments. In one embodiment, the siRNA is an EGFR siRNA. In one embodiment, the transcription factor decoy molecule is an NF-kB transcription factor decoy molecule. In one embodiment, the transcription factor decoy molecule is a STAT 3 transcription factor decoy molecule. In one embodiment, the deoxyribonucleic acid vector comprises a cytomegalovirus promoter sequence and a herpes simplex virus thymidine kinase sequence (pCMV-TK).

In one embodiment, the present invention contemplates a method comprising, a) providing: i) a patient exhibiting at least one symptom of a disease; ii) an ultrasound targeted microbubble population stably binding a plurality of nucleic acids; and iii) an ultrasound device capable of directing said microbubble population to said target cells; b) administering said microbubble population to said patient under conditions such that the at least one symptom of a disease is reduced.

In one embodiment, the administering further comprises using said ultrasound device to direct said microbubble population to said target cells. In one embodiment, the administering further comprises bursting said directed microbubble population under conditions such that a transgenic target cell is created. In one embodiment, at least one of the conditions is the ultrasound device operating at approximately 1.3-1.4 MHz. In one embodiment, the transgenic target cell expresses said plurality of nucleic acids. In one embodiment, the nucleic acids are selected from the group including but not limited to oligonucleotide therapeutic molecules, siRNA, shRNA, RNAi, miRNA, antisense, transcription factor decoy molecules, deoxyribonucleic acid vectors, genes, and gene fragments. In one embodiment, the siRNA is an EGFR siRNA. In one embodiment, the transcription factor decoy molecule is an NF-kB transcription factor decoy molecule. In one embodiment, the transcription factor decoy molecule is a STAT 3 transcription factor decoy molecule. In one embodiment, the deoxyribonucleic acid vector comprises a cytomegalovirus promoter sequence and a herpes simplex virus thymidine kinase sequence (pCMV-TK).

In one embodiment, the present invention contemplates a kit, comprising: a) a first container comprising an ultrasound targeted microbubble population; b) a second container comprising a plurality of nucleic acids; and c) a set of instructions to stably bind said ultrasound targeted microbubble population to said plurality of nucleic acids. In one embodiment, the nucleic acids are selected from the group consisting of oligonucleotide therapeutic molecules, siRNA, shRNA, RNAi, miRNA, antisense, transcription factor decoy molecules, deoxyribonucleic acid vectors, genes, and gene fragments. In one embodiment, the siRNA is an EGFR siRNA. In one embodiment, the transcription factor decoy molecule is an NF-kB transcription factor decoy molecule. In one embodiment, the transcription decoy molecule is a STAT 3 transcription factor decoy molecule. In one embodiment, the deoxyribonucleic acid vector comprises a cytomegalovirus promoter sequence and a herpes simplex virus thymidine kinase sequence (pCMV-TK). In one embodiment, the stably bound nucleic acids are deoxyribonuclease-resistant. In one embodiment, the stably bound nucleic acids are ribonuclease-resistant. In one embodiment, the stably bound nucleic acids are resistant to repetitive washings. In one embodiment, the microbubble population comprises a mixture of 1,2-distearoyl-sn-glycero-3-ethylphosphocholine (DSEPC), distearoylphosphatidyl-choline (DSPC), and PEG-40. In one embodiment, the mixture is a 7:14:1 mixture. In one embodiment, the microbubble population comprises a mechanical index of approximately 1.6. In one embodiment, the microbubble population comprises a bursting threshold at approximately 1.3-1.4 MHz.

DEFINITIONS

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

The term "biocompatible", as used herein, refers to any material does not elicit a substantial detrimental response in the host. There is always concern, when a foreign object is introduced into a living body, that the object will induce an immune reaction, such as an inflammatory response that will have negative effects on the host. In the context of this invention, biocompatiblity is evaluated according to the application for which it was designed: for example; a bandage is regarded a biocompatible with the skin, whereas an implanted medical device is regarded as biocompatible with the internal tissues of the body. Preferably, biocompatible materials include, but are not limited to, biodegradable and biostable materials.

The term "biodegradable" as used herein, refers to any material that can be acted upon biochemically by living cells or organisms, or processes thereof, including water, and broken down into lower molecular weight products such that the molecular structure has been altered.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the teen "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The teen "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the term "stably binding" or "stably bound" refers to any complexation between a first molecule and a second molecule that is not dislodged, disrupted, cleaved, and/or dissociated, etc. by normal physiological conditions. Such stable binding may be identified by testing including but not limited to protection from enzymes (e.g., a nuclease and/or protease) and/or repetitive washing (i.e., for example, between approximately 3-8 times) that may optionally include vortexing or centrifugation.

As used herein, the term "transcription factor" refers to any molecule capable of binding to a deoxyribonucleic acid promoter region. Generally, this binding results in either an upregulation or a downregulation of the downstream coding region controlled by the promoter region. Transcription factors are usually short protein sequences including but not limited to STAT sequences (e.g., STAT 3) or NF-kB sequences.

As used herein, the term "transcription factor decoy molecule" refers to any molecule capable of preventing the binding and/or function of a transcription factor. Transcription factor decoy molecules are usually short nucleic acid sequences that bind at genomic transcription factor binding sites (i.e., for example, an NF-kB transcription factor decoy molecule and/or a STAT 3 transcription factor decoy molecule).

As used herein, the term "sonoporation" refers to any ultrasound induced enhancement of cell membrane permeability, either with or without the presence of microbubbles.

As used herein, the term "microbubble" refers to any spherical arrangement of lipids creating an outer shell and an inner void space. The lipid layer may be modified to bind molecules in a stable manner.

As used herein, the "mechanical index" refers to any index of acoustic energy being delivered to a composition (i.e., for example, a tissue or a microbubble). Mathematically, a mechanical index is equal to the acoustic pressure (mPa) divided by the square root of the ultrasound frequency. UMTD microbubbles may have a mechanical index ranging between approximately 0.25-2.5, preferably between 0.5-2.0, more preferably between 0.75-1.75, but most preferably between 1.0-1.5. For example, a mechanical index of UMTD microbubbles may be approximately 1.6.

As used herein, the "bursting threshold" refers to any acoustic frequency that results in the lipid shell breakdown of a microbubble population, thereby releasing the stably bound nucleic acids. Such acoustic frequencies are usually generated by an ultrasound device operating at a frequency ranging between approximately 0.25-5 MHz, preferably between approximately 0.5-2.5 MHz, but more preferably between approximately 0.75-2.0 mHz, and most preferably between 1.0-1.5 MHz. For example, a bursting threshold of UMTD microbubbles may be approximately between 1.3-1.4 MHz.

As used herein, the terms "siRNA" refers to either small interfering RNA, short interfering RNA, or silencing RNA. Generally, siRNA comprises a class of double-stranded RNA molecules, approximately 20-25 nucleotides in length. Most notably, siRNA is involved in RNA interference (RNAi) pathways and/or RNAi-related pathways. wherein the compounds interfere with gene expression.

As used herein, the term "shRNA" refers to any small hairpin RNA or short hairpin RNA. Although it is not necessary to understand the mechanism of an invention, it is believed that any sequence of RNA that makes a tight hairpin turn can be used to silence gene expression via RNA interference. Typically, shRNA uses a vector stably introduced into a cell genome and is constitutively expressed by a compatible promoter. The shRNA hairpin structure may also cleaved into siRNA, which may then become bound to the RNA-induced silencing complex (RISC). This complex binds to and cleaves mRNAs which match the siRNA that is bound to it.

As used herein, the term "microRNA", "miRNA", or "µRNA" refers to any single-stranded RNA molecules of approximately 21-23 nucleotides in length, which regulate gene expression miRNAs may be encoded by genes from whose DNA they are transcribed but miRNAs are not translated into protein (i.e. they are non-coding RNAs). Each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to downregulate gene expression.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

An oligonucleotide sequence which is a "homolog" is defined herein as an oligonucleotide sequence which exhibits greater than or equal to 50% identity to a sequence, when sequences having a length of 100 bp or larger are compared.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., $C_0$ t or $R_0$ t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

The term "transfection" or "transfected" refers to the introduction of foreign DNA into a cell.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligodeoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists. J. Sambrook et al. (1989) In: *Molecular Cloning: A Laboratory Manual*, Cold Spring Harbor Press, NY, pp 9.31-9.58.

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligodeoxyribonucleotide probe or DNA probe to detect RNA species complementary to the probe used. Northern blots are a standard tool of molecular biologists. J. Sambrook, J. et al. (1989) supra, pp 7.39-7.52.

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligoribonucleotide probe or RNA probe to detect DNA species complementary to the ribo probe used.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

BRIEF DESCRIPTION OF THE FIGURES

FIG. 3 presents exemplary data showing immunofluorescent staining with Green Fluorescent Protein (GFP) in murine tumors 3 days after intravenous delivery of pEGFP-C1 bound to microbubbles and treatment with ultrasound (Panels A, B) or no ultrasound (Panel C). GFP positive staining was seen both in hollow structures (Panel A) as well as individual tumor cells (Panel B) in UMTD treated tumors.

FIG. 5. Post mortem histological analysis of tumors after intravenous delivery of either pCMV-TK (Panels A,C,D) or pEGFP-C1 (Panel B)-loaded microbubbles and treatment with ultrasound and GCV. Panels A and B illustrate the acellular zones (see arrows) visible under H&E stain. Panel C presents a merged image of two sister slides, one stained by Heoscht 33342 (blue overlay), and one stained by H&E. Panel D is a representative slide demonstrating variable vWF staining in acellular zones (arrows).

FIG. 21 presents exemplary data showing the binding characteristics of EGFR siRNA to a microbubble population.

Lanes 1 represent 100% binding of NF-κB to the radiolabeled probe, as obtained by excluding the competitor from the incubation mixture.

Figure 23:
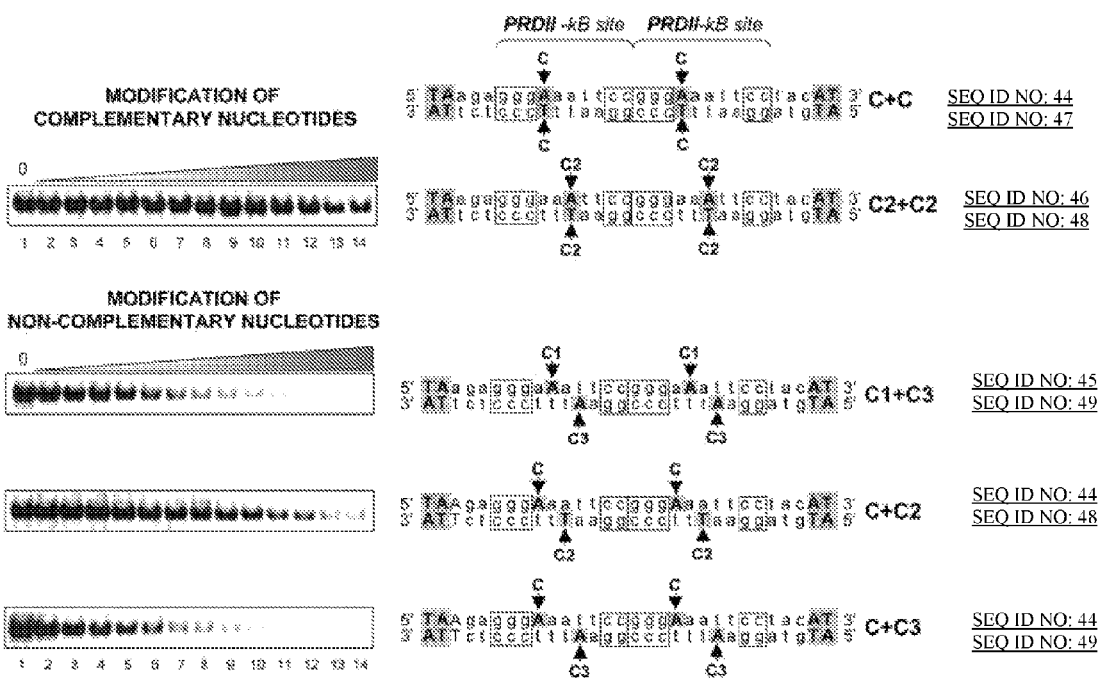

FIG. 23 illustrates an embodiment for the design of NF-kB transcription factor decoy molecules containing internal LNA substitutions on both strands and competition of these molecules for binding of NF-κB. LNA ODNs with internal substitutions on both strands were obtained by annealing oligomers containing LNAs in position C, C1, C2 of the sense strand with oligonucleotides containing LNAs in position C, C2, C3 of the antisense strand to generate the double-stranded molecules shown in the figure. LNA substitutions involved either complementary (C+C and C2+C2) or non-complementary (C1+C3, C+C2 and C+C3) nucleobases. Lower case, DNA monomers; bold upper case in grey, LNA bases. The ability of NF-κB to bind these molecules was tested in gel shift competition experiments as described in Materials and Methods. Only the protein/probe complex is shown. Competitor concentrations in lanes 2-14 were 38, 57, 85.8, 128.7, 193, 289.6, 434.4, 651.5, 977, 1466, 2200, 3300 and 4950 nM. In lanes 1, 100% binding of NF-κB to the radiolabeled probe is shown as determined by exclusion of the competitor from the incubation mixture.

DETAILED DESCRIPTION OF THE INVENTION

This invention is related to the field of gene and molecular therapeutics. Some embodiments of the present invention provide ultrasound/microbubble targeted delivery (UMTD) of genes that slow tumor growth. For example, in a mouse model of squamous cell carcinoma (SCC-VII) UMTDs delivered a Herpes Simplex Virus type 1 Thymidine Kinase (TK) gene to tumors as a suicide gene. Other medical conditions may be treated with UMTD by delivering oligonucleotide therapeutic molecules (e.g., transcription factor decoy molecules).

DNA binding microbubbles were prepared from a mixture of 1,2-distearoyl-sn-glycero-3-ethylphosphocholine, distearoylphosphatidyl-choline, and PEG-40 in PBS containing 1 mM EDTA. This mixture was placed in a glass vial, the head space was replaced with perflourobutane gas, and amalgamated. Resulting microbubbles were then washed several times and resuspended in PBS/EDTA, resulting in a microbubble concentration of 1–4×10^9 MB/ml and diameter of 1.9-2.3 □m. Plasmid DNA was attached by mixing plasmid (100 □g) with microbubbles and briefly vortexing.

In one embodiment, the present invention contemplates a method for administering a UMTD population as a targeted drug delivery platform to diseased tissues. For example, a UMTD population delivers the suicide gene TK to tumor cells. Although it is not necessary to understand the mechanism of an invention, it is believed that the suicide gene TK creates a transgenic tumor cell, wherein the expression of TK ultimately decelerates tumor growth. The data presented here establish proof of concept in tumor biology but is also highly suggestive that such therapies is of equal value to most any diseases or medical conditions that may be treated by targeted gene therapy. In other embodiments, microbubble carriers are a useful non-viral vectors with inherent targeting properties by virtue of their unique acoustic behavior in an ultrasound field.

I. Conventional Gene Therapy

Gene therapy has been reported as capable of destroying tumor cells in a variety of cancers, but requires improvements in delivery techniques to enable clinical application (Thomas and Grandis 2009). For example, the suicide gene, herpes simplex virus-1 thymidine kinase (TK), in conjunction with ganciclovir (GCV), has been studied for gene therapy of cancer in several clinical trials (Rainov 2000; Shand et al. 1999). These studies are disadvantaged by the requirement for surgical access to inject gene vectors directly into the tumor, which is not always technically feasible and limits the possibility of multiple treatments. Alternatively, if viral gene therapy vectors are delivered systemically, transduction of nontarget tissues may occur, resulting in adverse side effects (Parryl et al. 2009). Viral vectors also elicit an immune response which can limit their effectiveness and prevent repeated delivery (Nayak and Herzog 2010). An ideal gene therapeutic approach would be non-viral based, and capable of specifically targeting and destroying tumor cells after systemic delivery, while leaving non-target organs unaffected.

II. Contrast Microbubble Mediated Drug Delivery

Ultrasound contrast agents, gas-filled microspheres (microbubbles) encapsulated by a biocompatible shell, are emerging as new drug delivery system that may overcome some of the limitations of viral gene delivery systems (Chen et al. 2010; Villanueva 2009). In particular, such work has been directed towards the delivery of gene therapy vectors. However, most any nucleic acid composition is compatible with the system described herein, including but not limited to siRNA, shRNA, and/or antisense nucleic acids.

Much of the pioneering work using microbubbles to deliver nucleic acids was performed using microbubbles and UMTD to deliver genes at the DNA level, although the mechanisms underlying this delivery are still incompletely understood. Several groups have reported that the combined effects of microbubbles and ultrasound can alter cellular membranes, resulting in increased cellular permeability to both high and low molecular weight molecules. UMTD can also induce jetting and/or high velocity fragmentation, which may be another possible pathway of macromolecule internalization (Zhao et al. 2005). Although DNA can transgress the endothelial layer in vivo when delivered by microbubbles and UMTD, the mechanism of transgression is unclear and may involve a mix of the mechanisms involved in direct cellular uptake. The phenomenon on endothelial transgression may not be as critical in tumors, as many tumors (including SCC) often have abnormal vasculature, with large fenestrations and a high percentage of non-endothelialized vessels. Taken together, such data suggest that delivery of siRNA is likely to be a result of enhanced permeability of cell membranes due to ultrasound effects of the cell membrane in the presence of microbubbles.

In one embodiment, the present invention contemplates a method comprising a therapeutic delivery of siRNA. Although it is not necessary to understand the mechanism of an invention, it is believed that siRNA delivery has several advantageous differences versus the delivery of genes and/or plasmid DNA. Firstly, siRNA is a much smaller molecule than plasmid DNA. Because of this, once siRNA crosses the plasma membrane as a therapeutic molecule it can diffuse throughout the cell. The limited diffusion of plasmid DNA can be the rate limiting step of transduction in some systems. Shen et al., DNA diffusion in mucus: effect of size, topology of DNAs, and transfection reagents. Biophys J 2006; 91: 639-644. Secondly, because of the small size of siRNA, higher number of molecules can be loaded onto microbubbles compared to plasmid DNA, despite the fact that these microbubbles package less nucleic acid by weight. (Carson). Thirdly, siRNA can mediate knockdown effect both in the cytoplasm and in the nuclease (Whitehead), so the molecules are active immediately upon delivery. Lastly, siRNA is less stable than DNA and the knockdown mediated by siRNA can on the order of days due to natural RNA degradation (Whitehead). The data presented herein uses Silencer Select® siRNA, which is modified to increase the stability of the siRNA. The use of siRNA loaded microbubbles and UMTD also allows serial administration and demonstrates a unique advantage of the microbubble/UMTD system.

Contrast microbubbles are generally considered in the art as encapsulated gas-filled spheres with a diameter of less than 10 μm. Such size limitation allows the microbubbles to be injected into the bloodstream and freely circulate prior to elimination by lung and liver. Microbubbles are generally considered to be relatively safe and nonimmunogenic, and because of their transient nature they may have a decreased risk of oncogenicity.

Contrast microbubbles have been used for imaging because they exhibit enhanced acoustic backscatter in a nonlinear manner, thereby producing a complex "signature" that can be separated from tissue echoes. This capability has been enhanced with agents such as Optison® and Definity® that facilitated cardiac imaging technology, in particular visualization of the left ventricular cavity and/or wall motion of the heart, as well as allowed an overall assessment of tissue perfusion.

Microbubbles are also used in echocardiographic imaging as erythrocyte 'tracers' that transit through the circulation (Jayaweera et al. 1991; Kaul 2008). The contrast enhancement created by the microbubbles during clinical ultrasound imaging is based on their acoustic activity whereby the microbubbles expand and contract, or rupture, in response to ultrasound (Becker and Burns 2000; de Jong et al. 2002). More recently, this acoustic behavior of ultrasound contrast agents has been exploited for therapeutic purposes, and a number of studies have shown that microbubbles carrying genes on their surface facilitate transduction when ultrasound is externally applied as the microbubbles transit through the target site microcirculation (Bekeredjian et al. 2003; Chappell and Price 2006; Chen et al. 2007; Chen et al. 2010; Fujii et al. 2009).

The use of microbubbles as gene vectors is based on the hypothesis that destruction of DNA-loaded microbubbles by a focused ultrasound beam during their microvascular transit through the target area will result in localized transduction upon disruption of the microbubble shell, while sparing non-targeted areas. Ultrasound/Microbubble Targeted Delivery (UMTD) has been used to deliver genes to cells in vitro, and more recently, has been employed to deliver genes in vivo to treat diabetes and cardiovascular disease in experimental animal models (Chen et al. 2007; Chen et al. 2010; Fujii et al. 2009). Because this non-invasive, site-specific, non-viral approach to gene delivery could have significant value for treating tumors, we tested the general hypothesis that UMTD-mediated gene delivery can be used to treat solid tumors. Specifically, we investigated whether UMTD-mediated delivery of the suicide gene TK to tumors, in conjunction with GCV treatment, retards tumor growth in a mouse model of squamous cell carcinoma. Reporter gene studies were first performed to confirm transduction and develop the ultrasound treatment protocol. These were followed by proof of concept studies in which the TK gene was delivered via UMTD and the effect on tumor growth was assessed.

In some embodiments, the present invention contemplates improvements in contrast microbubble technology. In one embodiment, the improved microbubble technology comprises targeted drug delivery systems. For example, tissue inflammation may be detected by microbubble-targeted delivery of compounds including but not limited to VCAM-1, ICAM-1, and/or selectins. Alternatively, gene therapy may be achieved by targeting specific cells with the microbubble to selectively create transgenic diseased cells. For example, a microbubble binding a VEGF receptor can be used to detect angiogenesis in cancerous tissue.

In some embodiments, the microbubbles are gene or molecular therapy vectors. Until the present invention, the art has been limited to using commercially available microbubbles resulting in unpredictable success. Although it is not necessary to understand the mechanism of an invention, it is believed that conventional microbubbles only bind a maximum of 10% of DNA to which they are exposed. Consequently, the "loading factor" of conventional microbubbles is low and inefficient. Despite these clinically relevant disadvantages, conventional microbubbles have been used to deliver genes to a variety of tissues. Chen et al., "Reversal of streptozotocin induced diabetes in rats by gene therapy with betacellulin and pancreatic duodenal homeobox-1" *Gene Therapy* 14:1102 (2007); Hayashi et al., "Effect of sonoporation on cationic liposome-mediated IFN-beta gene therapy for metastatic hepatic tumors of murine colon cancer" *Cancer Gene Ther.* 16:638 (2009); and Li et al., "Optimising ultrasound-mediated gene transfer (sonoporation) in vitro and prolonged expression of a transgene in vivo: potential applications for gene therapy of cancer" *Cancer Lett.* 273:62 (2009).

The use of microbubbles as gene vectors has advantages over viral systems. During UMTD, intravenously injected microbubbles can be destroyed as they transit through the microcirculation of the target site where the ultrasound beam is directed, functionally achieving selective payload delivery without the need for invasive approaches such as direct intratumor injection. The lipid microbubbles we used for UMTD have no viral proteins, and can theoretically be administered repetitively. Additionally, because the microbubbles are ultrasound contrast agents, it is possible to simultaneously image microbubble transit through the tumor, thereby enabling more precise real time guidance of plasmid delivery.

The mechanisms underlying UMTD-mediated gene transfer are incompletely understood. While it is clear that ultrasound-induced destruction of the plasmid-bearing microbubbles is a necessary event, it not certain how or if the genes transgress the endothelial barrier following microbubble destruction. Christiansen and colleagues reported intravital imaging of rat cremaster microcirculation during UMTD of microbubbles bearing fluorescently labeled DNA, in which DNA deposition was observed to be perivascular in location with only 10-15% of the depositions associated with microvascular hemorrhage (Christiansen et al. 2003). Independent of gene release, UMTD can induce changes in the membranes of treated cells, leading to sporadic capillary ruptures and/or increased peiineability to macromolecules (Meijering et al. 2009; Price et al. 1998; van Wamel et al. 2004). Microbubble disruption at ultrasound frequencies used in our study can produce high local pressure currents (jetting) or high velocity fragmentation of the microbubble shell, which may also contribute to the transduction event (Zhao et al. 2005). Taken together, such data suggest that microporation of the vessel wall and/or enhanced permeability of cell membranes may be a mechanism for transfection by UMTD. While Christiansen (2003) observed a small portion of DNA deposition to anatomically co-localize with microvascular hemorrhage with UMTD, and others have posited ultrasound-microbubble induced microvascular hemorrhage as a mechanism for drug or particle delivery (Price et al. 1998) using very different ultrasound and in vivo testing conditions compared to ours, we did not observe microvascular hemorrhage in our study.

III. Microbubble Nucleic Acid Binding Capabilities

In some embodiments, the custom-design microbubbles described herein are capable of delivering large amounts of nucleic acids by incorporating positively charged lipids into the microbubble shell. The resulting microbubble formulation efficiently bound nearly 100 mg DNA per $1 \times 10^9$ microbubbles, which is significantly higher compared with reports of others (Hayashi et al. 2009; Maeda et al. 2009). Importantly, unlike naked plasmids which are quickly degraded by blood DNAses upon vascular administration, the data presented herein shows that the plasmid on the microbubble surface was shielded from digestion by DNAse. The DNAse protection would indicate a close and tight binding of the DNA to the microbubble, which is supported by ethidium bromide staining studies (data not shown) demonstrating DNA association with microbubble shell (i.e., for example, deoxyribonuclease resistant and/or ribonuclease resistant). It is expected that the negatively charged plasmid DNA would preferentially associate with the cationic lipid heads in these microbubbles. Although it is possible that there might be some burial of the plasmid under the lipid heads, it is unlikely that the hydrophilic DNA would preferentially reside in close proximity with the hydrophobic core of a microbubble. Furthermore, because plasmid DNA may be added to the formulation after the microbubbles have already been synthesized, it is unlikely that plasmid DNA would be "trapped" in the gas filled interior of a microbubble.

In one embodiment, a microbubble capable of binding nucleotide sequences (i.e., for example, DNA) was prepared from a mixture of 1,2-distearoyl-sn-glycero-3-ethylphosphocholine (DSEPC), distearoylphosphatidyl-choline (DSPC), and PEG-40 in PBS containing 1 mM EDTA. This solution was then amalgamated with perflourobutane to form microbubbles, which were washed and resuspended in PBS/EDTA, resulting in a microbubble concentration of $1-4 \times 10^9$/ml and diameter of 1.9-2.3 μm as measured by Coulter counting. Plasmid DNA was attached by mixing plasmid (100 μg) and $1 \times 10^9$ microbubbles and briefly vortexing. To achieve maximal microbubble perfusion and gene delivery, imaging and UMTD were combined using a two-transducer system to perform low power two-dimensional imaging and high power microbubble destruction, respectively. Microbubble perfusion was visualized in real time using 14 MHz ultrasound at low acoustic power and ContrastPulse Sequencing (Sequoia, Siemens). Upon visualization of microbubbles within the tumor, microbubbles were burst using an orthogonally placed ultrasound transducer (Sonos 7500, Philips, Andover, Mass.) delivering ultrasound at 1.3 MHz and a mechanical index of 1.6. Destructive ultrasound bursts were repeated each time that microbubble replenishment of the tumor was visualized, which typically ranged from 1-3 seconds. The number of ultrasound frames per burst cycle, typically 3 to 6 frames, was also adjusted to the minimum number that destroyed the vast majority of the microbubbles in the ultrasound field. Using this system, a working model was developed that was shown to be effective at transducing mouse tumor tissue with reporter genes on intravascular microbubbles and have delivered a therapeutic gene, which slowed tumor growth significantly.

In one embodiment, conventional microbubbles may be structurally improved to bind DNA and respond to acoustic stimuli. For example, most reports describing the use of microbubbles for gene therapy are "home made" and do not bind DNA efficiently. While some researchers have added cationic lipids to increase DNA binding, none have performed systematic tests to maximize binding to the levels reported herein by discovering proper lipid proportionality ratios. For UMTDs, a proper response to ultrasound administration is equally important. Target tissues should be fully perfused prior to the start of the burst sequence and to confirm that microbubbles are ruptured during that sequence. In one embodiment, real-time monitoring of perfusion and bursting is performed to control for inter-animal variation in burst sequencing. In one embodiment, the present invention contemplates, a hybrid ultrasound system that is capable of delivering and monitoring acoustic response using two different frequencies of ultrasound.

Figure 1A:
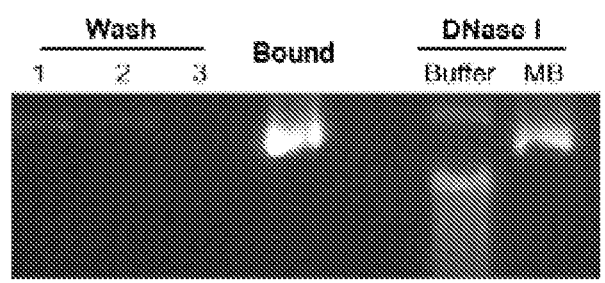
FIG. 1A. DNA content by agarose gel electrophoresis demonstrating efficient DNA binding to microbubble (lanes 1-4) and resistance of DNA bound to microbubbles against digestion by DNAses (lanes 5 and 6). Microbubbles loaded with DNA were washed 3 times to remove unbound DNA (wash lanes 1-3). Microbubbles were destroyed and bound DNA was recovered ("Bound", lane 4). DNA suspended in reaction buffer ("Buffer", lane 5) or loaded onto microbubbles ("MB," lane 6)) was challenged by DNAase I.
Figure 1B:
FIG. 1B presents exemplary data showing agarose gel electrophoresis demonstrating efficient DNA binding to microbubble and lack of plasmid release over time. Microbubbles loaded with DNA were washed immediately to remove unbound DNA (0 hours), and washed again at 1, 2, 4, and 8 hours post attachment (the washes are in lanes 2-6). Washed microbubbles were destroyed and bound DNA was recovered after all washes were complete at 8 hours ("Bound", lane 7). Lane 1 contains 500 ng plasmid as a loading control.
Figure 1C:
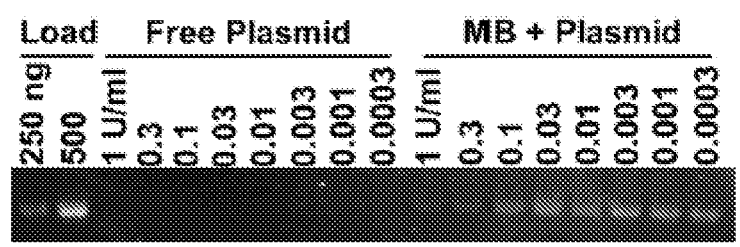
FIG. 1C presents exemplary data showing agarose gel electrophoresis demonstrating the resistance of DNA bound to microbubbles against digestion by DNAses. Microbubbles loaded with DNA were washed 3 times to remove unbound DNA and subjected to a range of DNAase I concentrations from 0.0003 units/ml to 1 unit/ml (lanes 11-18). As a control, free plasmid DNA was also challenged with DNAase I at these same concentrations (lanes 3-10). Lanes 1 and 2 contain 250 ng and 500 ng plasmid as loading controls.

As most conventional microbubbles used for gene therapy are not designed specifically for UMTD, some embodiments of the present invention contemplate custom-design microbubbles capable of binding and delivering large amounts of DNA by incorporating positively charged lipids into a microbubble shell. In one embodiment, a custom design microbubble binds approximately 100 μg DNA per $1 \times 10^9$ microbubbles. This binding efficiency is a significantly higher DNA incorporation as compared with reports of others using commercially available contrast agents. See, FIG. 1A. When analyzed by gel electrophoresis, there was minimal DNA in the washes performed after the attachment procedure, indicating a strong association between microbubbles and plasmid DNA. Plasmid DNA attached to microbubbles was also protected from DNAse I digestion under conditions that efficiently digest free DNA, indicating that DNA might be shielded from digestion by DNAses in blood upon vascular delivery. See, FIG. 1A, lanes 1-3 and lanes 5-6, respectively. In one embodiment, exposing microbubbles to larger amounts of DNA resulted in similar levels of DNA loading, indicating that microbubbles approach saturation at this concentration. By gel electrophoresis, there was minimal DNA in the washes performed shortly after the attachment procedure, with no plasmid release over a 4 hour period and minimal release up to 8 hours later. See, FIG. 1B. Plasmid DNA attached to microbubbles was also protected from DNAse I digestion at concentrations much greater than that required for the complete digestion of uncomplexed plasmid DNA. See, FIG. 1C.

IV. Creation of Transgenic Diseased Cells

In one embodiment, the present invention contemplates compositions comprising custom microbubbles (MBs) and ultrasound (US) to deliver reporter genes to tumors in vivo A population of custom designed microbubbles comprising bound DNA were infused into the jugular vein of mice in conjunction with ultrasound-mediated microbubble delivery to the tumor site (e.g., the total infusion time and target delivery time was approximately 20-30 minutes). Microbubble perfusion of the tumor was visualized in real time using a 14 MHz imaging transducer at a low acoustic power to minimize microbubble destruction (Contrast Pulse Sequencing, Sequoia, Siemens). Upon visualization of microbubbles within the tumor, microbubbles were burst using an orthogonally placed ultrasound transducer (Sonos 7500, Philips) delivering ultrasound at 1.3 MHz and a mechanical index of 1.6, with the 14 MHz imaging transducer confirming successful microbubble destruction. Thereafter, the venous cannula was removed where subsequent cell transformation and transgene expression was allowed for 3 days before analysis.

A. Luciferase Gene Transfection

Prior to performing therapeutic studies, luciferase genes were delivered to tumors in order to quantify transgene expression. Using the ultrasound exposure cell transduction conditions described herein, a level of luciferase expression was measured that is consistent with other reports of UMTD gene delivery to other organ systems when microbubbles are delivered systemically. Bekeredjian et al., 2003. The data presented herein demonstrates that specific targeting is achieved by navigation of the ultrasound beam, as there was minimal reporter gene transduction in non-insonified tissues. Furthermore, the control group receiving only DNA-loaded microbubbles had very little tumor expression of luciferase, underscoring the importance of the ultrasound in transduction.

Figure 2:
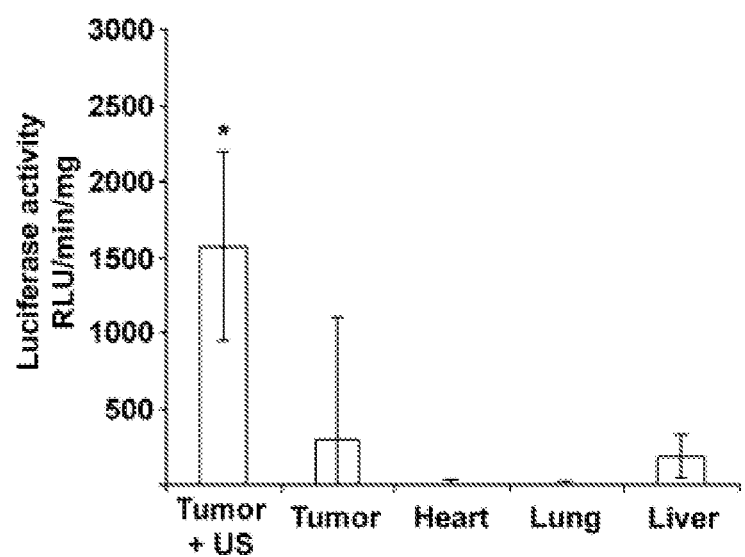
FIG. 2 presents exemplary luciferase activity in murine squamous cell carcinoma and control tissues 3 days following intravenous delivery of pCMV-luc bound to microbubbles. Mice from the Tumor+US sample were treated with ultrasound directed to the tumor. Non-targeted heart, lung and liver samples were obtained from the ultrasound treated mice, and control tumor samples were obtained from a separate group receiving plasmid-loaded microbubbles but no ultrasound. (*$P<0.02$)

Using the ultrasound exposure conditions described herein as capable of creating transgenic tumor cells, luciferase activity in tumors was significantly greater in 6 mice receiving microbubbles binding pCMV-Luc vectors delivered by UMTD (1568±627 RLU/min/mg), as compared to 5 control mice receiving microbubbles binding pCMV-Luc vectors without delivery by UMTD (294±807 RLU/min/mg, $p=0.02$). Tumor luciferase activity in the mice receiving pCMV-Luc loaded microbubbles and ultrasound delivery to the tumor was also significantly higher than activity in non-insonified tissues obtained from these same mice ($p<0.02$). See, FIG. 2. These data indicate that UMTD mediated targeting and cell transformation with delivered DNA fragments was much greater and efficient than conventional drug delivery methods.

B. Green Fluorescent Protein Reporter Gene Transfection

The data presented herein also demonstrate that GFP reporter genes can determine what cell types were transduced, and identified transduction in two classes of cells. See, FIG. 3. Many GFP positive cells were located in and around areas which by DAPI nuclear staining, appeared to comprise the walls of hollow structures resembling vasculature ranging in diameter from 25 µm to over 100 µm. FIG. 3A Also, a small number of tumor cells stained positive for GFP, accounting for less than 1% of the total number of tumor cells. FIG. 3B. Tumors from the control group not receiving UMTD displayed no GFP staining, either in structures appearing vascular or in the general tumor cell population. FIG. 3C. Likewise, non-insonified, non-tumor tissue obtained from mice injected with GFP plasmid loaded microbubbles and treated with tumor directed UMTD displayed no GFP staining (data not shown).

These data identified GFP transduction both in tumor cells and cells bordering acellular areas displaying a vascular morphology, many of which correspond to the acellular zones which were abundant in the TK/GCV treated group (infra). Although the staining of these zones for the vascular markers vWF and Griffonia Simplicifolia Lectin I was variable, approximately 90% of these structures stained positive upon in vivo injection of Heoscht dye, indicating anatomic continuity with the systemic circulation. FIG. 5. A pattern of positive staining for perfusion with negative staining for endothelium is not unusual for tumor vasculature and it is likely that many of these structures were conduits for blood and microbubbles at the time of transduction (Bhattacharya et al. 2008). The GFP data thus indicate both vascular as well as direct cellular transduction, which is consistent with the intravital microscopic observations of DNA deposition reported by Christiansen and colleagues (2003).

C. Transgenic TK Tumor Cells and GCV Treatment

In one embodiment, the present invention contemplates a method for treating malignant tumors comprising administering an intravenous injection of plasmid-loaded microbubbles and delivering the microbubbles to a designated target site with an ultrasound device.

Some studies have used UMTD-mediated gene therapy in an attempt to treat solid tumors via a direct intratumor injection followed by ultrasound delivery. Chen et al. 2009a; Chen et al. 2009b, and Li et al. 2009. This invasive approach, however, does not take advantage of the non-invasive nature of systemic microbubble injection combined with local ultrasound to achieve targeted delivery. Another report described using an adenovirus virus loaded microbubbles and ultrasound to treat tumors. Greco et al. 2010. However, it is well known that the use of viral vectors may be immunogenic and less advantageous relative to a purely non-viral delivery system (i.e., for example, a UTMB drug delivery system).

Delivery of HSV-1 TK and treatment with ganciclovir slows tumor growth. Mice (n=6) received intravenous microbubbles loaded with pCMV-TK (or pEGFP-C1 in controls) and were treated with UMTD. Both groups were administered GCV (80 mg/kg) IP daily commencing 3 days after UMTD and continuing until mice were euthanized. Tumor volume was serially measured using ultrasound.

Figure 4:
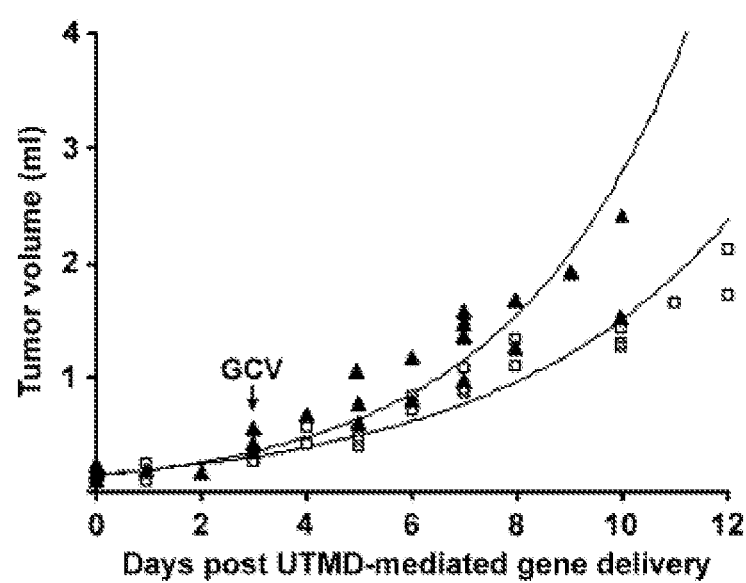
FIG. 4. Growth of murine tumors after intravenous injection of either pCMV-TK (□) or pEGFP-C1 (▲)-loaded microbubbles and treated with ultrasound. Daily ganciclovir (GCV) injections began on day 3. Best fit lines were calculated from all data points in each group assuming an exponential growth curve (TK $R2=0.94$; GFP $R2=0.91$).

These data suggest that UMTD can direct delivery of the suicide gene thymidine kinase (TK) to carcinoma cells, ultimately resulting in deceleration of tumor growth in a murine model of squamous cell carcinoma. See, FIG. 4.

These data illustrate tumor growth following transduction of the GCV-treated mice receiving UMTD-gene delivery of pCMV-TK (TK/GCV group) or pEGFP-C1 (GFP/GCV group) from an initial size of 0.1-0.15 ml (Day 0) until the mice were euthanized at a tumor volume of approximately 2 ml. Tumor growth rates were similar in both TK and GFP-treated mice from Days 0-3, and began to diverge at day 3, when GCV treatment was initiated. From days 3-10, the calculated doubling times of the TK/GCV treated tumors (3.4±0.2 days) was significantly greater than that of control GFP/GCV treated tumors (2.9±0.4 days; $p<0.02$). These findings establish proof of concept that UMTD can impact tumor biology. As such, the data suggests gene therapy-based treatments for cancer, supporting a potential role for microbubble carriers as non-viral vectors with inherent targeting properties by virtue of their unique acoustic behavior in an ultrasound field. These data suggested that plasmid-loaded microbubbles and an ultrasound protocol could effect a therapeutic change in tumor growth in a murine squamous cell carcinoma model. Upon UMTD-mediated delivery of the suicide gene herpes simplex virus thymidine kinase (TK), and treatment with GCV, there was a small but significant increase in the doubling time of TK/GCV treated tumors compared to GFP/GCV controls.

D. Histological Evaluation of Transgenic Tumors

In one embodiment, the present invention contemplates a method comprising administering a TK/GCV vector to create a transgenic tumor that is associated with increased acellular zones.

For example, murine tumors treated with UMTD mediated gene therapy were harvested for histological analysis. See, FIG. 5. H&E stains of tumor sections revealed diffuse areas of cell dropout in the TK-treated tumors. FIG. 5A. These acellular areas were significantly more numerous in the TK/GCV group than in the GFP/GCV controls (3.8±2.1/mm$^2$ vs 1.3±1.0/mm$^2$, $p<0.03$). FIG. 5B. This three-fold difference in the density of acellular zones occurred despite a comparable initial density of acellular zones in the 4 mice that were euthanized on day 3 following UMTD treatment (TK=0.2 zones/mm$^2$, GFP=0.2 zones/mm$^2$). The acellular zones stained negatively for Oil Red (fat), fibrosis (Gomori Trichrome), and lymphatic markers (LYVE-1). Most (~90%) of the acellular zones also stained negatively for the endothelium marker vWF (FIG. 5D) or the endothelium binding lectin Griffonia Simplicifolia Lectin I (GSLI) (data not shown). Hoescht 33342 stain injected intravenously just prior to euthanasia (e.g., ante-mortem) appeared in the periphery of these zones of clearing (e.g., acellular zones), indicating that most were connected to the systemic vascular circulation despite the fact that many such zones stained negatively for the presence of endothelium. FIG. 5C. Interestingly, many of these areas of apparent cell dropout (e.g., acellular zones) were very similar in morphology to areas that were GFP positive in our reporter gene transduction studies described above. FIG. 3A. The nearly four-fold increase in acellular zones in TK/GCV treated mice developed despite comparable initial densities of acellular zones in the 4 mice that were euthanized on day 3 following treatment (TK=0.2 zones/mm$^2$, GFP=0.2 zones/mm$^2$), and may point to an important mechanism of growth inhibition. Conceivably, the zones of clearing are remnants of vasculature destroyed by TK/GCV treatment. The enlargement of the structures, as well as their increase in number, could also represent the dropout of anatomically contiguous TK/GCV-treated microvascular and tumor cells that have been subsequently removed by the circulation. This effect would be further augmented by the "bystander effect," which may enlarge these zones through the leakage of phosphorylated GCV through gap junctions into neighboring tumor cells (Rainov 2000; Aoi et al. 2008). Given that the Hoescht stains demonstrated access of these zones to the systemic circulation, there is a strong possibility that killed cells were cleared into the circulation. As control tumors also demonstrated acellular zones, albeit significantly fewer, it is unlikely that all of these areas represented treatment-specific cellular dropout; some may represent tumor vasculature. FIG. 5. TUNEL staining revealed a modest (~1.5 fold) but statistically significant increase in apoptosis throughout TK/GCV treated tumors compared to controls which could also contribute to the overall growth inhibition.

Figure 6A:
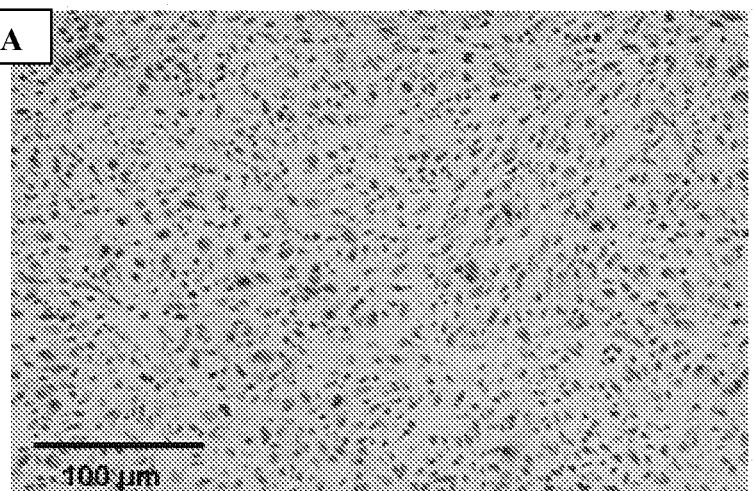
FIG. 6. Post mortem TUNEL assays from murine tumors after intravenous injection of either pCMV-TK (Panel A) or pEGFP-C1 (Panel B)-loaded microbubbles and treatment with ultrasound and GCV.
Figure 6B:
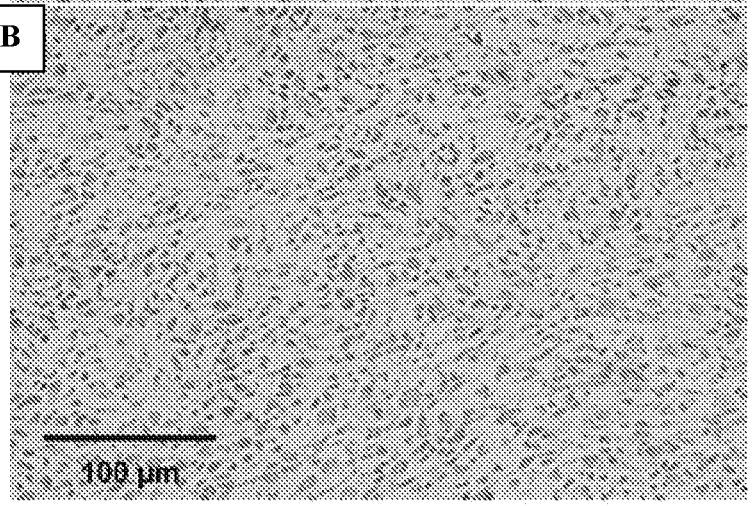

Although it is not necessary to understand the mechanism of an invention, it is believed that TK/GCV gene therapy increases tumor cell apoptosis. Murine tumors treated with UMTD mediated gene therapy were harvested for TUNEL assay. Additionally, TUNEL assay indicated that TK/GCV treated mice had more apoptotic nuclei than control GFP/GCV treated mice (6±1 vs 4±1; p=0.04). See, FIG. 6A and FIG. 6B, respectively This increase in apoptosis could contribute to, but unlikely account entirely for, the overall growth inhibition. Although it is not necessary to understand the mechanism of an invention, it is believed that one possibility remains that apoptosis predominated earlier in the course of the tumors, when transgene expression would be highest, as the tissue was sampled late after treatment. Nonetheless, these mechanisms are likely not mutually exclusive, and a combination of the factors discussed above may have contributed to overall growth inhibition.

In one embodiment, the present invention contemplates a method comprising microbubble mediated gene therapy for mediating gene transfer into solid tumors. Control experiments have shown that little transduction occurs in the absence of UMTD, and little transgene expression in a non-target tissue.

The data show that treatment of solid tumors with TK/GCV resulted in a significant reduction in tumor growth rate. For example, growth rate reduction began at day 3, which corresponds to TK expression and GCV administration. TK/GCV treatment increased the density of acellular structures. These acellular structures are contiguous with the greater circulation and might represent cellular dropout TK/GCV treatment increases apoptosis.

Future studies should further investigate the mechanisms underlying the efficacy of UMTD, which in turn will inform strategies for maximizing gene transduction and optimizing the therapeutic effects of this new technology.

V. EGFR siRNA Microbubble Therapeutics

Strategies targeting Epidermal Growth Factor Receptor (EGFR), including the use of RNA interference, have shown great promise to treat carcinoma, but would likely benefit from improved delivery techniques. Microbubble contrast agents have the ability to specifically deliver nucleic acids to target tissues when treated with specific ultrasound parameters that mediate ultrasound-targeted microbubble destruction (UMTD). Custom designed microbubbles efficiently bound high levels of siRNA and mediated protection from RNAse A. Delivery of anti-EGFR siRNA to squamous cell carcinoma cells in vitro resulted in 70% knockdown of EGFR expression and UMTD mediated delivery of anti-EGFR siRNA slowed EGF dependent growth by over 50%. Serial UMTD mediated delivery of anti-EGFR siRNA in vivo inhibited tumor growth during the treatment period in a murine model of subcutaneous squamous cell carcinoma, with the doubling time of anti-EGFR treated tumors (5.40+/−1.77 days) being significantly longer than control groups where no siRNA was delivered (2.16+/−0.27 days) or where a control siRNA was delivered by UMTD (2.19+/−0.46 days) (p=0.01). This reduction in growth rate corresponded to a significant decrease in EGFR expression after microbubble-mediated siRNA delivery, as assayed by immunofluorescence and western blot. These data indicate that custom designed microbubbles and UMTD can deliver siRNA to tumors, resulting in tumor growth suppression. Microbubbles and UMTD are a promising system for siRNA delivery that may direct organ-specific therapeutic RNA inhibition across a spectrum of disease states amenable to gene regulation.

In one embodiment, the present invention contemplates a method for using custom designed microbubbles binding to therapeutic EGFR siRNA, wherein an ultrasonic device can drive the microbubbles to the intended target and burst these microbubbles for local delivery of the EGFR siRNA. Subsequently, a transgenic tumor cell results wherein the transgenic tumor cell has a reduced expression of EGFR. Such treatment in murine tumors resulted in reduced EGFR expression and a concomitant slowing or stopped tumor growth. These data establish proof of concept that custom designed microbubbles and UMTD can deliver siRNA to tumors and this delivery is sufficient to effect tumor biology. In other embodiments, microbubbles comprise nonviral carriers of siRNA with the ability to greatly affect gene expression in a specific tissue and the capacity for multiple treatments.

A. Epidermal Growth Factor Receptor (EGFR)

The inhibition of Epidermal Growth Factor Receptor (EGFR) signaling is an established strategy for treating cancer. As such, many drugs and agents have been developed to block growth factor binding, block receptor dimerization, decrease EGFR expression, or reduce downstream kinase activity. Several pharmaceutical agents such as the monoclonal antibody Cetuximab (Bonner) and the kinase inhibitor Gefitinib (Kirby) inhibit EGFR signaling and have progressed through clinical trials. Despite their promise, these treatment regimes are often limited by their off target effects and the concept of EGFR inhibition would likely benefit from a targeted noninvasive delivery system. Targeted delivery both increases the local dosage and on-target activity while simultaneously decreasing off target activity in vulnerable organs and tissues. The use of RNA interference in treating solid tumors has also shown efficacy in some systems (Lai, Zhang). Although these studies illustrate the potential and potency of EGFR inhibition, they are disadvantaged by the requirement for access to directly inject genes or gene vectors into the tumor, which is not always technically feasible. Viral vectors are among the most efficient gene delivery agents, but the use of viral vectors limits the possibility of multiple treatments (Cross). Delivery of genes that express RNAi is limited by the inefficiency of DNA transduction, which can be a limiting factor with nonviral systems, especially those that do not involve a direct injection (Carson). The direct injection of antisense RNA or siRNA is attractive, but is often of limited utility because of ubiquitous RNAse activity. An ideal therapeutic approach would be capable of delivering the therapeutic payload to tumor tissue, specifically targeting and inhibiting the expression of EGFR in tumor cells after systemic delivery, and also be amiable to multiple treatments.

Microbubble contrast agents, along with ultrasound, are emerging vector systems that are capable of binding a variety of nucleic acids and may overcome some of the limitations of current siRNA delivery systems (Carson 2011; Chen et al. 2010; Villanueva 2009). The use of microbubbles as nucleic acid delivery vectors is based on the observation that the bursting of therapeutic microbubbles via UMTD results in localized deposition of microbubble shell components and the hypothesis that if these microbubble shells carry a therapeutic agents, the therapeutic effect would be limited to the insonified area. This phenomenon has been exploited to deliver reporter genes both in vitro and in vivo. UMTD has also been used to deliver therapeutic genes to pancreatic islets and squamous cell carcinoma in mice (Carson et al 2011; Chen et al. 2007; Chen et al. 2010; Fujii et al. 2009). As UMTD has been demonstrated to have value for treating tumors through the delivery of DNA (Carson et al 2011), the general hypothesis was tested in that UMTD-mediated delivery of siRNA can treat tumors more efficiently. Towards this end, the hypothesis was tested that UMTD-mediated delivery of anti-EGFR siRNA will inhibit squamous cell carcinoma growth in vivo. In vitro and in vivo studies were first performed to confirm downregulation of EGFR in our system. Following these studies, anti-EGFR siRNA loaded microbubbles were delivered to tumors via UMTD and tumor growth was serially measured.

B. siRNA Binding by Custom Designed Microbubbles

Figure 21A:
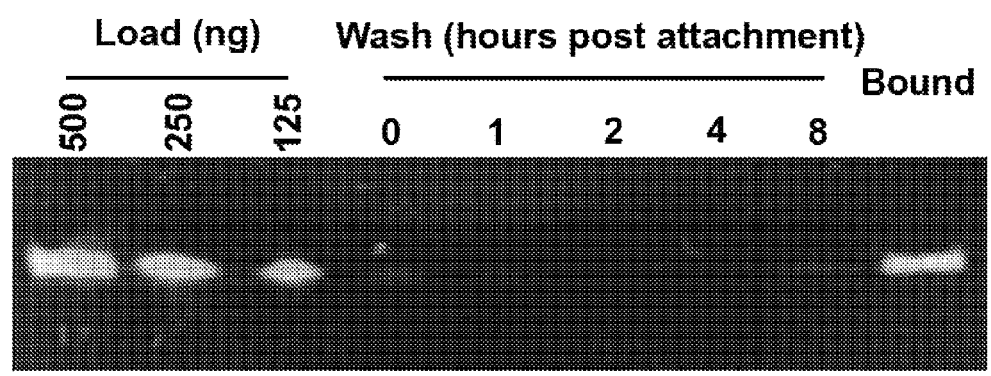
FIG. 21A: Acrylamide-urea gel electrophoresis showing efficient siRNA binding to microbubbles (MB) and lack of siRNA dissociation from the MB over time. MB loaded with siRNA were washed immediately to remove unbound siRNA (0 hours) and washed again at 1, 2, 4, and 8 hrs post attachment (washes in lanes 4-8). Washed MB were destroyed and bound siRNA was recovered after washes were complete at 8 hrs ("Bound", lane 9). Lanes 1-3 have 500, 250, and 125 ng siRNA as loading controls.
Figure 21B:
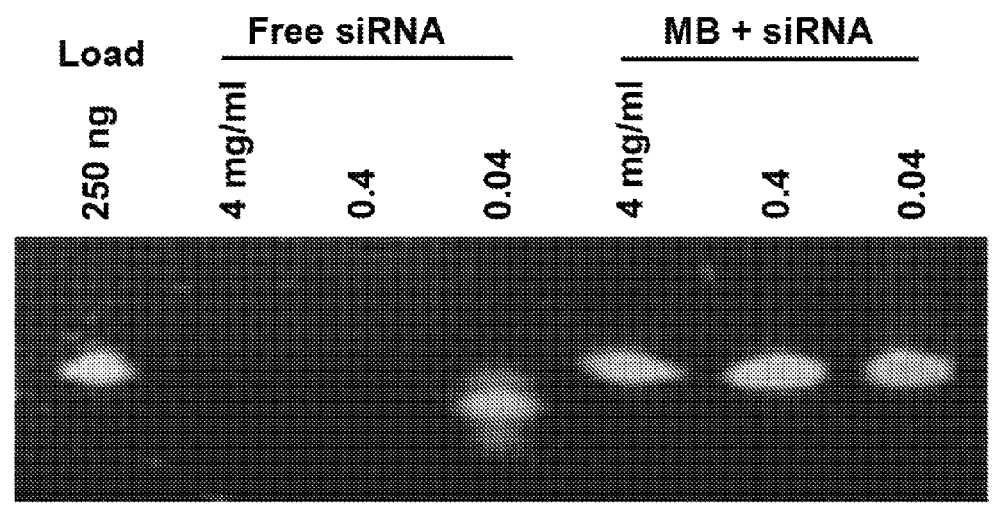
FIG. 21B shows the lack of susceptibility of the bound EGFR siRNA to a microbubble population to RNAase.

The microbubble formulation bound ~7 µg RNA per $1 \times 10^9$ microbubbles. Larger amounts of siRNA mixed into lipid microbubble components prior to amalgamation resulted in similar levels of siRNA binding, indicating saturation of RNA loading system. Little siRNA dissociation was seen up to 8 hours post attachment. FIG. 21A, lanes a-d. Microbubble association also protected siRNA from RNAse A digestion, and RNAse A concentration sufficient for complete digestion of uncomplexed siRNA. FIG. 21B, lanes a-b.

C. EGFR Knockdown in Squamous Cell Carcinoma Cells In Vitro

Figure 15:
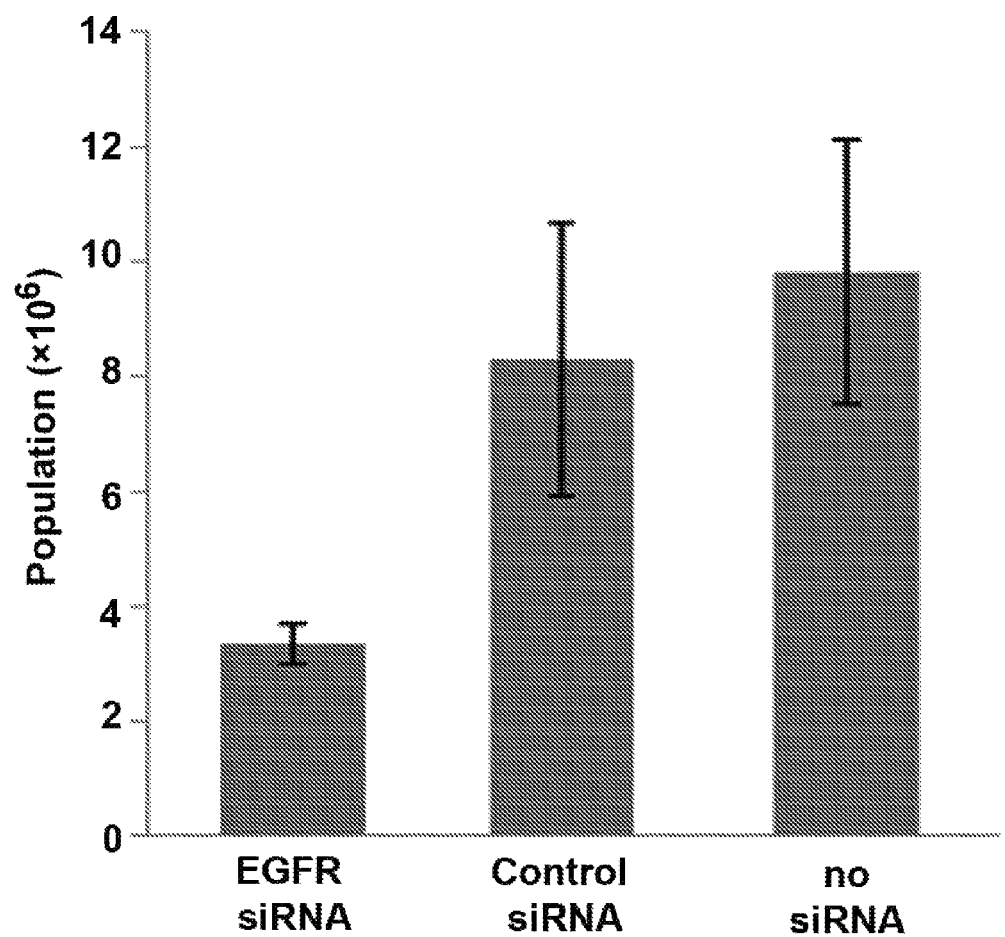
FIG. 15 presents exemplary sonoporation siRNA data showing the reduction in tumor cell population (Y axis) with either: 1) EGFR siRNA; 2) Control siRNA; or 3) No siRNA.
Figure 16A:
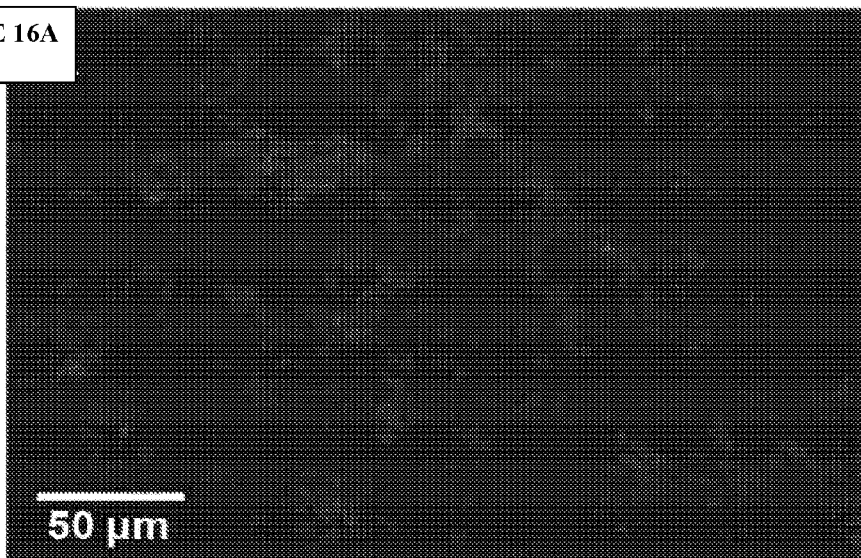
FIG. 16 presents exemplary immunofluorescence data in Control (A) and Treated (B) conditions demonstrating EGFR knockdown in tumors.
Figure 16B:
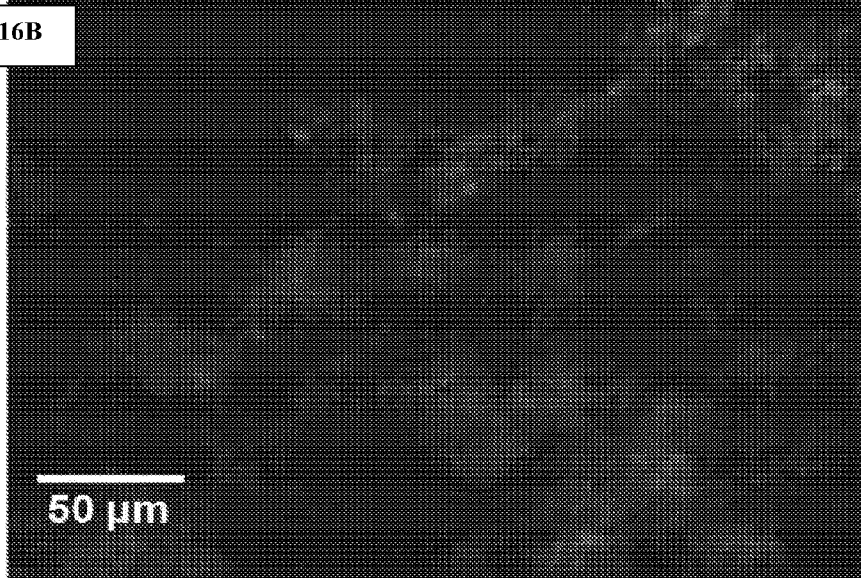

Silencer Select® siRNA designed to silence EGFR, was able to repress the expression of EGFR by 70% after lipofectamine transfection into SCC-VII cells compared to cells transfected with control siRNA. See, FIG. 15. Microbubble and UMTD mediated delivery of EGFR siRNA efficiently reduced EGF dependant growth by over two fold for two days following sonoporation, consistent with functional inhibition of EGFR in vitro. See, FIG. 16. These data confirmed knockdown of EGFR by siRNA in tissue culture following transfection of SCC cells with Silencer Select® EGFR siRNA using lipofectamine transfection in vitro. EGFR siRNA reduced EGFR expression by 70% in tissue culture, consistent with other reports of Silencer Select® siRNA activity. Additionally, microbubble and ultrasound mediated delivery of EGFR siRNA to SCC cells strongly inhibited growth under conditions where growth is dependent upon supplemental EGF. These data support the strong growth inhibitory effects of EGFR inhibition, which has been previously reported.

D. EGFR Knockdown in Murine Tumors

Figure 17:
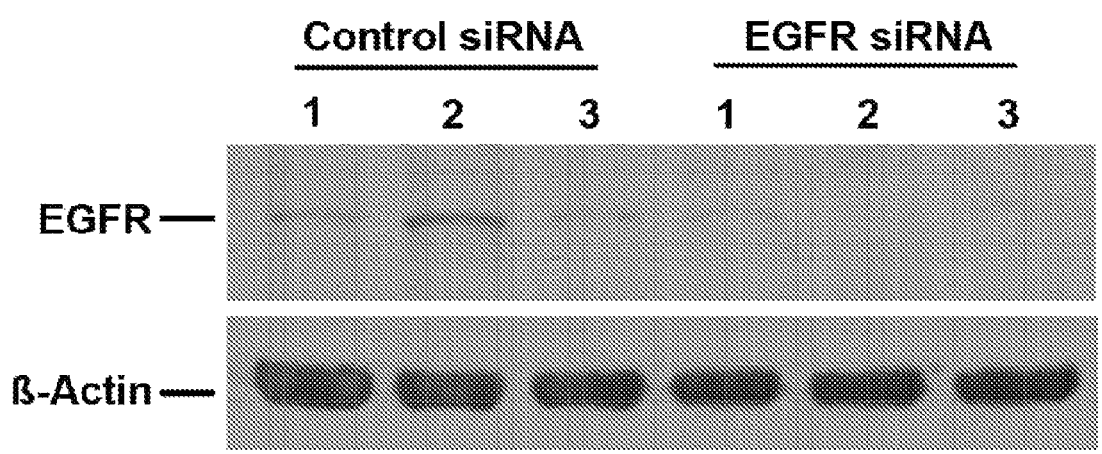
FIG. 17 presents exemplary Western Blot gel electrophoresis data showing EGFR knockdown in tumors in the presence of Control siRNA (lanes 1-3) and EGFR siRNA (lanes 4-6). β-Actin was added to all lanes as an internal control standard.
Figure 18:
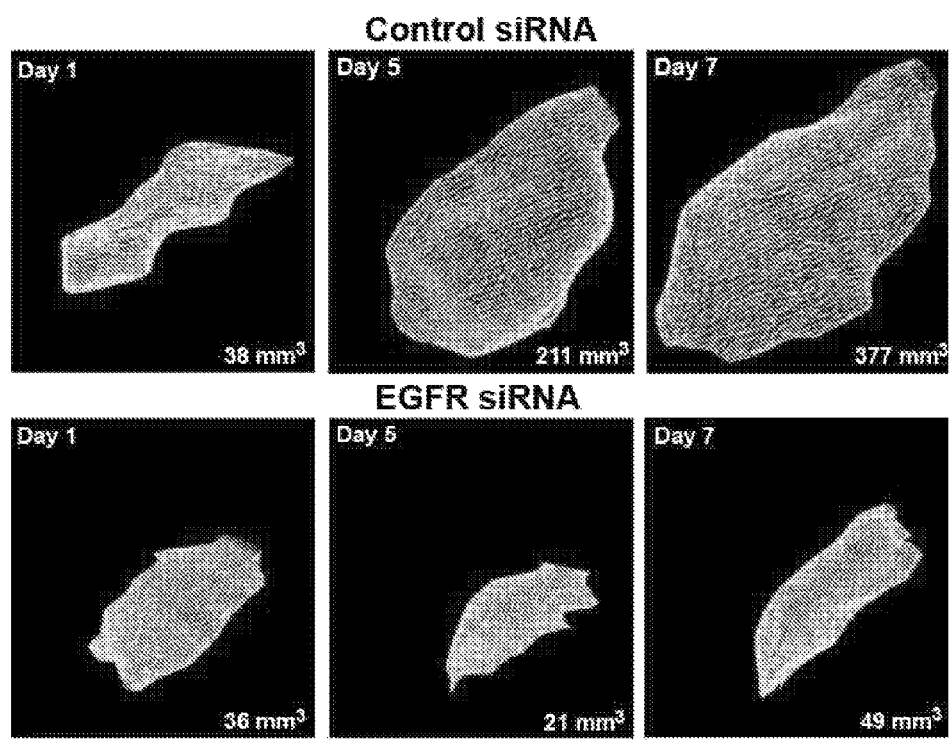
FIG. 18 presents representative immunofluorescence data comparing tumor growth on Day 1, Day 5 and Day 7 after administration of Control siRNA microbubbles or EGFR siRNA microbubbles. It can be seen that the effect of EGFR siRNA microbubbles demonstrates a reduced growth of approximately 10-fold.

Delivery of EGFR siRNA in vivo reduced the expression of EGFR as assayed by immunofluorescence. See, FIG. 17. EGFR knockdown was disturbed widely throughout the tumor in these slides, and was not predominantly localized to the capsule of these tumors indicating the treatment could effectively reach the core of the tumor. Western blot analysis also indicates a strong, though, somewhat inconsistent knockdown of EGFR expression. See, FIG. 18.

E. Delivery of Anti-EGFR siRNA Inhibits Tumor Growth In Vivo

The effect of microbubble and UMTD mediate siRNA delivery to murine tumors in vivo was determined. Beginning approximately two days after UMTD-mediated delivery of EGFR siRNA, there was a slowing, stopping (and in some cases reversal) of tumor growth in EGFR siRNA treated mice while control siRNA treated tumors grew at an exponential rate. This tumor growth suppression was continued up until, and after, the second treatment and strong growth inhibition was still seen several days after the second treatment. All together, there was a more than two fold increase in the doubling time of treated tumors compared to controls where either empty microbubbles or negative control siRNA loaded microbubbles were delivered. This severe retardation in growth was maintained throughout the treatment period in anti-EGFR siRNA treated mice, with some (4/7) treated tumors returning to steady growth an average of 6 days after the last treatment and some (3/7) never returning to a pattern of steady growth. The treatment effect delayed the time to reach a critical volume by several days. It should be noted that while some (4/7) anti-EGFR treated tumors did achieve critical volume, the majority (3/4) of these mice developed ulcerated tumors and treated mouse that did not achieve critical volume developed an ulcer as well. This is in contrast with only 1 out of 14 control tumors that developed ulcerations throughout their much shorter period of tumor growth.

Figure 19:
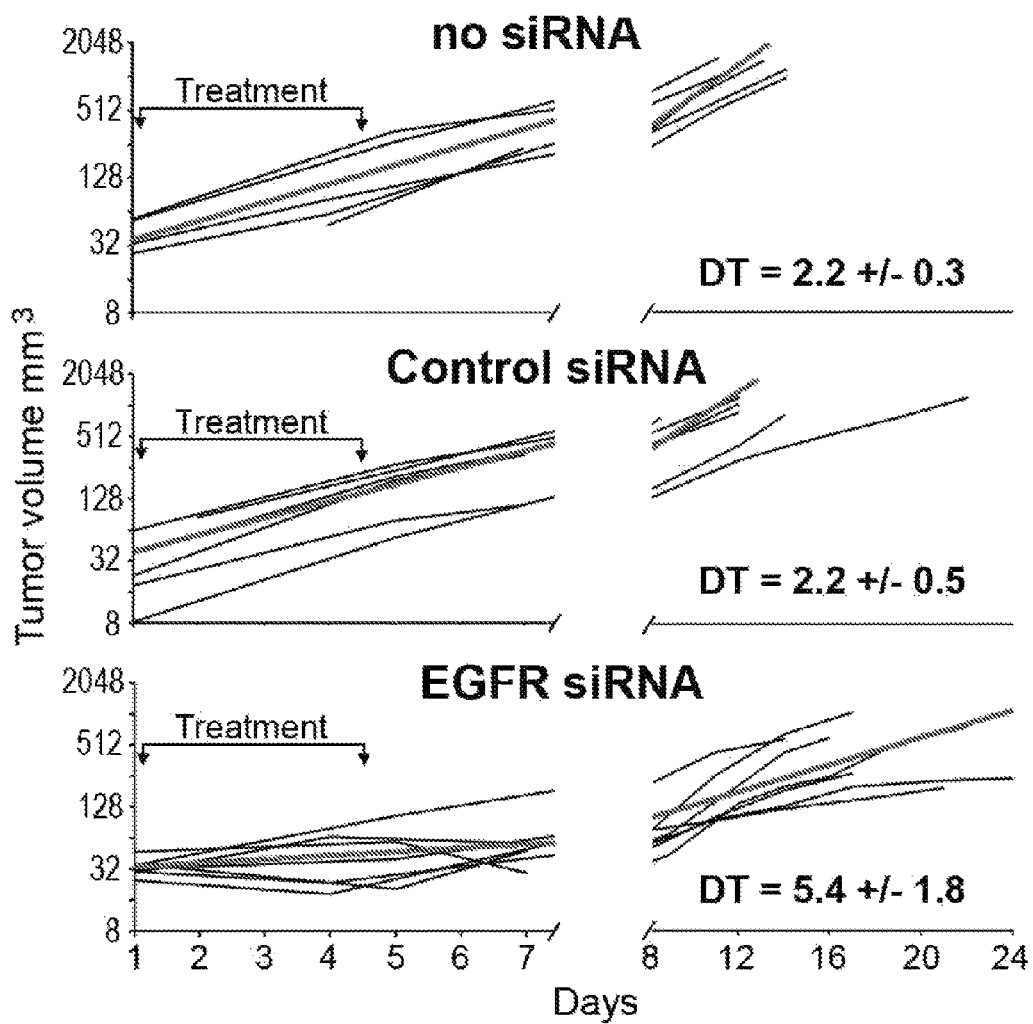
FIG. 19 presents individual tumor growth data after administration of No siRNA microbubbles, Control siRNA microbubbles, or EGFR siRNA microbubbles. The tumor growth rate is significantly reduced after administration of EGFR siRNA microbubbles.

Specifically, tumor growth was monitored following UMTD mediated delivery of microbubbles loaded with either anti-EGFR siRNA (A), empty microbubbles (B), or control siRNA loaded microbubbles (C). See, FIG. 19. Tumor volumes of anti-EGFR siRNA MB treated mice grew to an average volume of 0.082 (±0.054) ml by 8-10 days after initial treatment. Control mice treated with empty MB, control siRNA loaded MB, or anti-EGFR loaded MB in the absence of UMTD grew to 0.52 (±0.20) ml, 0.48 (±0.24) ml, and 0.50 (±0.16) ml respectively. These differences in tumor volume between treatment and control groups are statistically significant with p=0.003 (anti-EGFR MB vs empty MB), p=0.015 (anti-EGFR MB vs control siRNA), and p=0.048 (anti-EGFR MB+UMTD vs anti-EGFR MB-UMTD). On average, control tumors grew from an average size of initial size of approximately 0.03 ml to over 1 ml in less than 2 weeks after microbubble injection and UMTD treatment was initiated. Treated mice, on average, took more than twice as long to grow to large sizes. In treated mice, there was almost no growth during the treatment period and the tumors of several (3/7) mice did not grow even after the treatment period was over. As such, the calculated doubling time of anti-EGFR treated tumors (5.40+/−1.77 days) was significantly longer than control groups where no siRNA was delivered (2.16+/−0.27 days) or where a control siRNA was delivered by UMTD (2.19+/−0.46 days) (p=0.01).

F. Delivery of Anti-EGFR siRNA Increases Time to Critical Volume In Vivo

Figure 20:
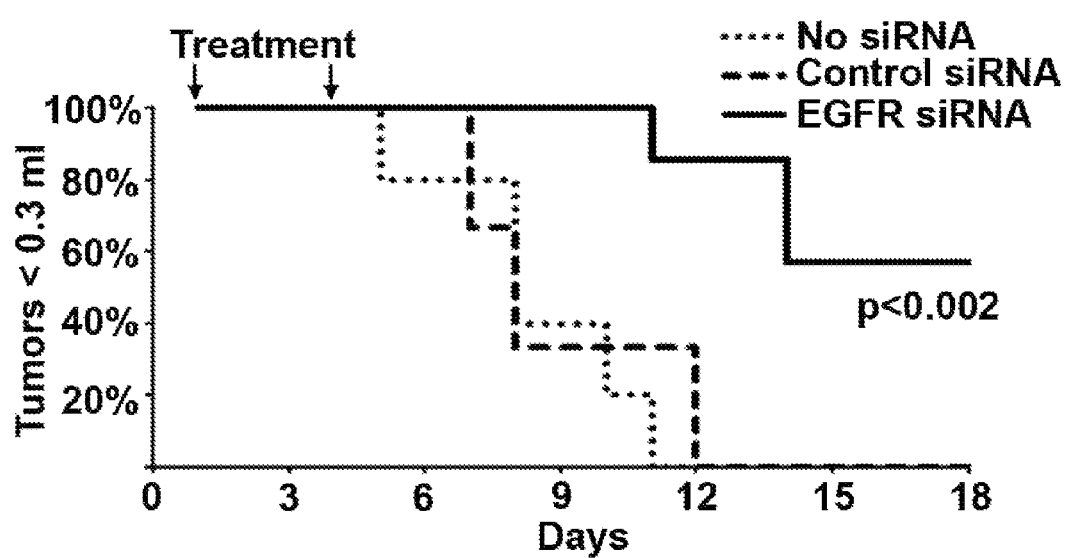
FIG. 20 presents exemplary data showing time to critical volume (~0.3 ml) of individual murine SCC tumors after intravenous injection of either no empty MBs (no siRNA), Control siRNA loaded microbubbles, or EGFR siRNA loaded microbubbles, and treatment with ultrasound on day 1 and day 4 or 5.

The time to critical volume (>0.3 ml) was determined following UMTD mediated delivery of microbubbles loaded with either anti-EGFR siRNA (A), empty microbubbles (B), or control siRNA loaded microbubbles (C). See, FIG. 20. Control tumors grew achieved critical volume at an average of 8.4+/−1 days after initial treatment. EGFR siRNA treated tumors achieved critical volume in an average of 18.7+/−2.2 days, with several (3/7) never achieving critical volume. These differences are significant with p<0.002.

The magnitude of tumor growth inhibition in the above data was much greater than that reported for perfused microbubbles delivering plasmid DNA and also greater than that has been reported for the alternate invasive approach using direct intra-tumor injection of DNA loaded microbubbles (Aoi et al. 2008; Nie et al. 2008). Although it is not necessary to understand the mechanism of an invention, it is believed that this increased efficacy might be due to the increased dose (at a molar level) of siRNA compared to plasmid DNA. It is also believed that the increased efficacy might also be due to the capacity of siRNA to mediate a therapeutic effect in the cytoplasm. The use of multiple treatment doses, which is an advantage of this minimally invasive, nonviral system, may have also increased efficacy considerably.

VI. Optimization of UTMB Methods

With further optimization of treatment parameters therapeutic results are likely to be enhanced beyond those data described herein. For example, it is likely that greater numbers of microbubbles could be delivered to the tumor by direct arterial cannulation of the tumor blood supply. Although direct cannulation is more invasive, it is possible that greater levels of transduction might make this approach attractive for tumors with easily identifiable and accessible arterial blood supplies. Furthermore, it is likely that TK/GCV is not the only gene to decrease tumor growth such that the attachment and delivery of other anti-cancer genes should be considered. It may well be that some alternative anti-cancer genes perform better than TK/GCV, while others may not be as effective. It should be noted that few anti-cancer drugs or treatments are very effective alone, and the small decrease in growth seen when our system is used in isolation could lead to greater growth inhibition when used as an adjuvant with other treatments.

It should be noted that since a histological evaluation of tumors at the time of euthanasia only sheds partial light on the mechanisms of growth inhibition that would have begun days earlier. Although it is not necessary to understand the mechanism of an invention, it is believed that apoptosis may have predominated earlier in the course of the tumors, when transgene expression would be expected to be highest. It is also believed that, when taken as a whole, anti-vascular effects, direct TK/GCV mediated cell killing, and any bystander effects, are not mutually exclusive, and all these mechanisms may have contributed to the totality of the observed tumor growth inhibition.

In some embodiments contemplated by the present invention, gene therapy uses microbubbles as vectors and ultrasound to direct local transfer of the genes to the target site. Although it is not necessary to understand the mechanism of an invention, it is believed that such methods may circumvent limitations and disadvantages of viral gene delivery systems. For example, by injecting microbubbles systemically, at least one embodiment described herein is minimally invasive and is easily adapted to serial treatments. It is further believed that an ability to specifically and selectively target treatment by manipulating the direction of an ultrasound beam provides an inherently more effective treatment option for non-resectable, inaccessible tumors, in which direct intra-tumor or intra-arterial injection of therapeutics is not technically feasible. The data presented herein establish an ability to modify the natural history of tumor growth with UMTD-directed gene therapy, and also provide insights into factors that may play a role in optimizing transduction under conditions of systemic microbubble injection.

VII. Oligonucleotide Therapeutics

In one embodiment, the present invention contemplates a microbubble population that can be useful for delivering all types of oligonucleotide therapeutics, including but not limited to, deoxyribonucleic acid (DNA) vectors, antisense, RNAi, miRNA, and/or transcription factor decoys In one embodiment, the present invention contemplates a microbubble population comprising transcription factor decoys. In one embodiment, the transcription factor decoys are bound to the microbubble population. In one embodiment, the transcription factor decoys comprise STAT 3 decoy molecules.

A. Transcription Factors

In molecular biology and genetics, a transcription factor (sometimes called a sequence-specific DNA-binding factor) may comprise a protein that binds to specific DNA sequences, thereby controlling the flow (or transcription) of genetic information from DNA to mRNA. Latchman D. S, "Transcription factors: an overview". *Int. J. Biochem. Cell Biol.* 29(12): 1305-1312 (1997); and Karin M., "Too many transcription factors: positive and negative interactions" *New Biol.* 2 (2): 126-131 (1990). Transcription factors are believed to perform this function alone or with other proteins in a complex, by promoting (as an activator), or blocking (as a repressor) the recruitment of RNA polymerase (the enzyme that performs the transcription of genetic information from DNA to RNA) to specific genes. Roeder R., "The role of general initiation factors in transcription by RNA polymerase II". *Trends Biochem. Sci.* 21(9): 327-335 (1996); Nikolov et al., "RNA polymerase II transcription initiation: a structural view" *Proc. Natl. Acad. Sci. U.S.A.* 94 (1):15-22 (1997); and Lee et al., "Transcription of eukaryotic protein-coding genes" *Annu. Rev. Genet.* 34: 77-137 (2000).

A defining feature of transcription factors is that they contain one or more DNA-binding domains (DBDs), which attach to specific sequences of DNA adjacent to the genes that they regulate. Mitchell et al., "Transcriptional regulation in mammalian cells by sequence-specific DNA binding proteins" *Science* 245 (4916): 371-378 (1989); and Ptashne et al., "Transcriptional activation by recruitment" *Nature* 386 (6625): 569-577 (1997). Some known examples of specific transcription factors are presented below. See, Table I.

TABLE I

Examples of specific transcription factors

| Factor | Structural type | Recognition sequence | SEQ ID NO: | Binds as |
|---|---|---|---|---|
| SP1 | Zinc finger | 5'-GGGCGG-3' | 1 | Monomer |
| AP-1 | Basic zipper | 5'-TGA(G/C)TCA-3' | 2 | Dimer |
| C/EBP | Basic zipper | 5'-ATTGCGCAAT-3' | 3 | Dimer |
| Heat shock factor | Basic zipper | 5'-XGAAX-3' | 4 | Trimer |
| ATF/CREB | Basic zipper | 5'-TGACGTCA-3' | 5 | Dimer |
| c-Myc | Basic-helix-loop-helix | 5'-CACGTG-3' | 6 | Dimer |
| Oct-1 | Helix-turn-helix | 5'-ATGCAAAT-3' | 7 | Monomer |
| NF-1 | Novel | 5'-TTGGCXXXXXGCCAA-3' | 8 | Dimer |

Walter F., PhD. Boron (2003). Medical Physiology: A Cellular And Molecular Approaoch. Elsevier/Saunders. pp. 125-126

B. Transcription Factors in Disease Development

Due to transcription factor roles in development, intercellular signaling, and cell cycle, some human diseases have been associated with mutations in transcription factors. Semenza, Gregg L. (1999). Transcription factors and human disease. Oxford [Oxfordshire]: Oxford University Press. ISBN 0-19-511239-3. Some transcription factors may result in pathogenic activity by either, activating or repressing transcription of a particular protein at the wrong time. For example, the family of signal transducers and activators of transcription factors (STAT factors) and NF-kB transcription factors have been implication is several disease conditions. Many transcription factors are either tumor suppressors or oncogenes, and, thus, mutations or aberrant regulation of them is associated with cancer. Three groups of transcription factors are known to be important in human cancer: 1) the NF-kappaB and AP-1 families; 2) the STAT family or 3) the steroid receptors. Libermann et al., "Targeting transcription factors for cancer gene therapy". Curr Gene Ther 6 (1): 17-33 (2006), See, Table II.

TABLE II

Representative Transcription Factors Causing Pathological Conditions

| Condition | Description | Locus |
|---|---|---|
| Rett syndrome | MECP2 transcription factor | Xq28 |
| Diabetes | Hepatocyte nuclear factors (HNFs) or insulin promoter factor-1 (IPF1/Pdx1) | multiple |
| Developmental dyspraxia | FOXP2 transcription factor | 7q31 |
| Autoimmune diseases | FOXP3 transcription factor | Xp11.23-q13.3 |
| Li-Fraumeni syndrome | Tumor suppressor p53 | 17p13.1 |
| breast cancer | The STAT family | multiple |
| multiple cancers | The HOX family | multiple |

The family of signal transducers and activators of transcription (STAT) play a central role in signaling by numerous cytokines, polypeptide growth factors, and oncoproteins. STATs were initially described in the context of regulating physiologic cell signaling contributing to such diverse processes as differentiation, proliferation, and apoptosis. An increasing number of studies have implicated STAT activation, particularly STAT 3, in transformation and tumor progression. Constitutive activation of STAT 3 has been detected in many hematopoietic and solid malignancies, including multiple myeloma, leukemias, lymphomas, mycosis fungoides, as well as carcinomas of the prostate, breast, lung, pancreas, ovary and head and neck. Gouilleux-Gruart et al., Blood, 87, 1692-1697 1996; Bowman et al., Proc. Natl. Acad. Sci. USA, 98, 7319-7324 2000; Grandis et al., Proc. Natl. Acad. Sci. USA, 97, 4227-4232. 2000; Huang et al., Gynecol Oncol, 79, 67-73. 2000; and Garcia et al., Oncogene, 20, 2499-2513 2001.

Upon activation, STAT proteins dimerize and translocate to the nucleus where they regulate gene expression by binding to specific DNA response elements. Darnell, Science, 277, 1630-1635 (1997). To address directly the role of STAT 3 as an oncogene, a constitutively active mutant of STAT 3 was generated (i.e., for example, STAT 3 C) and shown to induce transformation of fibroblasts and tumor formation in nude mice. Yu et al., Science, 269, 81-83 1995; and Bromberg et al., Cell, 98, 295-303 (1999). In addition to being a point of convergence for numerous oncogenic signaling pathways, STAT 3 also participates in cell growth and survival. One of the first indications that STAT 3 signaling contributes to malignancy, at least in part by preventing apoptosis, came from studies showing that increased expression of the antiapoptotic Bcl-2-family gene bcl-xL is dependent on constitutively activated STAT 3 in multiple-myeloma cells. Inhibition of STAT 3 signaling blocked the expression of Bcl-xL in these tumor cells and sensitized them to FAS-mediated apoptosis Catlett-Falcone et al., Curr. Opin. Oncol., 11, 490-496 (1999). Consistent with these findings, STAT 3 activation has been shown to regulate Bcl-xL expression and apoptosis in a wide range of tumor cells. Niu et al., Oncogene, 21, 2000-2008 (2002).

C. Transcription Factor Decoy Molecules as a Therapeutic

1. STAT Decoy Molecules

The association of STAT 3 activation with transformation and tumor progression suggests that STAT 3 may be an attractive molecular target for cancer therapy. Several strategies have been used to block the action of STAT proteins, including antisense methods, ectopic expression of dominant-negative mutants. Nakajima et al., EMBO J., 15, 3651-3658 (1996); Grandis et al., J. Natl. Cancer Inst., 90, 824-832 (1998); Li et al., J. Biol. Chem., 277, 17397-17405 (2002), inhibition of upstream kinases (Fry et al., Science, 265, 1093-1095 (1994); Turkson et al., Mol. Cell. Biol., 19, 7519-7528 (1999); Kraker et al., Biochem. Pharmacol., 60, 885-898 (2000), and phosphotyrosyl peptides (Turkson et al., J. Biol. Chem., 276, 45443-45455 (2001). An alternative approach to target the action of transcription factors, including STAT proteins, involves the use of double-stranded "decoy" oligonucleotides. The double stranded DNA decoy closely corresponds to the response element within the promoter region of a responsive gene. By achieving a sufficient concentration of decoy in the target cells, the authentic interaction between a transcription factor and its endogenous response element in genomic DNA is impaired, with subsequent modulation of gene expression. Nabel et al., Science, 249, 1285-1288 (1990).

STAT proteins perform the dual function of signal transduction and activation of transcription. STATs have been implicated in signaling by numerous cytokines, polypeptide growth factors, and oncoproteins. After activation, STAT proteins dimerize and translocate to the nucleus, where they bind to DNA-response elements and regulate gene expression. Darnell, J. E., Jr. (1997) Science 277, 1630-1635. STAT proteins were initially described in the context of regulating physiologic cell signaling, contributing to such diverse processes as differentiation, proliferation, and apoptosis. An increasing number of studies have implicated STAT activation, particularly STAT 3, in transformation and tumor progression. Bromberg, J. & Darnell, J. E., Jr. (2000) Oncogene 19, 2468-2473.

Cumulative evidence supports a central role for aberrant STAT signaling in oncogenesis. Constitutive activation of STAT 3 has been detected in many cancers, including, multiple myeloma, leukemias, lymphomas, mycoses fungoides, and brain, prostate, breast, lung, and head and neck cancers. Garcia et al. (2001) Oncogene 20, 2499-2513; Gouilleux-Gruart et al., (1996) Blood 87, 1692-169; Grandis et al., (2000) Proc. Natl. Acad. Sci. USA 97, 4227-4232; Huang et al., (2000) Gynecol. Oncol. 79, 67-73; and Bowman et al., (2000) Oncogene 19, 2474-2488. Cells stably transformed by the v-Src oncoprotein have been found to harbor activated STAT 3, thus linking STAT 3 activation to Src-mediated oncogenesis. Yu et al., (1995) Science 269, 81-83. To directly address the role of STAT 3 as an oncogene, a constitutively active mutant of STAT 3 was generated and shown to induce transformation of fibroblasts and tumor formation in nude mice. Bromberg et al., (1999) Cell 98, 295-303. Further investigation demonstrated that STAT 3-transfoimed fibroblasts were resistant to apoptotic stimuli, indicating that cancers characterized by STAT 3 activation may be less susceptible to chemotherapy and or irradiation. Shen et al., (2001) Proc. Natl. Acad. Sci. USA 98, 1543-1548. The association of STAT 3 activation with transformation and tumor progression suggests that STAT 3 may be an attractive molecular target for cancer therapy.

Several strategies have been used to block the action of STAT proteins, including: i) antisense methods, ectopic expression of dominant-negative mutants (Grandis et al., (1998) J. Clin. Invest. 102, 1385-1392; Nakajima et al., (1996) EMBO J. 15, 3651-3658; Li et al., (2002) J. Biol. Chem. 277, 17397-17405); ii) inhibition of upstream kinases (Fry et al., (1994) Science 265:1093-1095; Kraker et al., (2000) Biochem. Pharmacol. 60, 885-898; and Turkson et al., (1999) Mol. Cell. Biol. 19, 7519-7528.); or iii) phosphotyrosyl peptides (Turkson et al., (2001) J. Biol. Chem. 276, 45443-45455). An alternative approach to target the action of transcription factors, including oligonucleotides. The double-stranded DNA decoy closely corresponds to the response element within the promoter region of a responsive gene. By achieving a sufficient concentration of decoy in the target cells, the authentic interaction between a transcription factor and its endogenous response element in genomic DNA is impaired, with subsequent modulation of gene expression. Nabel Et al., (1990) Science 249, 1285-1288. This approach has been used successfully to target STAT 6 activation resulting in preferential restriction of IL-4-driven T helper 2 cell activity. Wang et al., (2000) Blood 95, 1249-1257.

A recent study evaluated the ability of a double-stranded decoy oligonucleotide based on the STAT 3 binding sequence, hSIE, to target activated STAT 3 in a relevant tumor model. Sadowski et al., (1993) Science 261, 1739-1744. Constitutive STAT 3 activation has also been demonstrated to be downstream of an epidermal growth factor receptor (EGFR) autocrine growth pathway in squamous cell carcinoma of the head and neck (SCCHN) in vitro and in vivo. Grandis et al., (2000) Laryngoscope 110, 868-874. Further investigation suggested that constitutive STAT 3 activation contributed to tumor growth independent of the EGFR autocrine axis in SCCHN and may therefore serve as a therapeutic target. Kijima et al., (2002) Cell Growth Differ. 13, 355-362. Although it is not necessary to understand the mechanism of an invention, it is believed that a STAT 3 decoy may inhibit the binding of phosphorylated STAT 3 dimers to the promoter region of STAT 3 target genes, thereby inhibiting STAT 3-mediated gene regulation. One study used cell lines established from patients with SCCHN to show that a STAT 3 decoy selectively binds to activated STAT 3 and blocks STAT 3-mediated gene transcription in these cancer cells. Treatment with the STAT 3 decoy formulation also inhibited the proliferation of SCCHN cells. By contrast, STAT 3 decoy treatment of normal oral cells has no effect on cell growth. Leong et al., PNAS 100(7): 4138-4143 (2003).

Sense and antisense strands of STAT 3 decoy and mutant control decoy oligonucleotides may be designed and/or obtained from MWG Biotech (High Point, N.C.). In one embodiment, a STAT 3 decoy sequence is 5'-CATTCCCG-TAAATC-3' (SEQ ID NO: 9), 3'GTA-AAGGGCATTTAC-5' (SEQ ID NO: 10). In one embodiment, a mutant control decoy sequence is 5'-CATTTCCTTAAATC-3' (SEQ ID NO: 11), 3'-GTAAAGGGAATT-TAG-5' (SEQ ID NO: 12). Other alternative mutant decoy sequences are presented below. See, Table III.

TABLE III

Sequences And Relative STAT 3-DNA Binding Affinities Of STAT 3 Decoy and Mutant Control Decoys

| SEQ ID NO(S): | | | Relative Binding to STAT 3 |
|---|---|---|---|
| 9, 10 | STAT 3 Decoy (hSIE) | 5'-CATTTCCCGTAAATC-3'<br>3'-GTAAAGGGCATTTAC-5' | ++++ |
| 13, 14 | SIE | 5'-CAGTTCCCTTAAATC-3'<br>3'-GTCAAGGGAATTTAG-5' | ++ |

| | Mutants of STAT 3 Decoy | | Number of Base Pair Mutations | |
|---|---|---|---|---|
| 15, 16 | Mutant 1 | 5'-CAGTTCCCGTAAATC-3'<br>3'-GTCAAGGGCATTTAG-5' | 1 | +++ |
| 17, 18 | Mutant 2 | 5'-CATTTCACGTAAATC-3'<br>3'-GTAAAGTGCATTTAG-5 | 1 | + |
| 19, 20 | Mutant 3 | 5'-CATTTCCCTTAAATC-3'<br>3'-GTAAAGGGAATTTAG-5' | 1 | − |
| 21, 22 | Mutant 4 | 5'-CATTTCCCGTCAATC-3'<br>3'-GTAAAGGGCAGTTAG-5' | 1 | ++ |
| 23, 24 | Mutant 5 | 5'-CAGTTCACGTAAATC-3'<br>3'-GTCAAGTGCATTTAG-5' | 2 | ++ |
| 25, 26 | Mutant 6 | 5'-CAGTTCCCGTCAATC-3'<br>3'-GTCAAGGGCAGTTAG-5' | 2 | + |
| 27, 28 | Mutant 7 | 5'-CATTTCACGTCAATC-3'<br>3'-GTAAAGTGCAGTTAG-5' | 2 | + |
| 29, 30 | Mutant 8 | 5'-CATTTCCCTTCAATC-3'<br>3'-GTAAAGGGAAGTTAG-5 | 2 | +++ |
| 31, 32 | Mutant 9 | 5'-CAGTTCACGTCAATC-3'<br>3'-GTCAAGTGCAGTTAG-5' | 3 | +/− |
| 33, 34 | Mutant 10 | 5'-CAGTTCCCTTCAATC-3'<br>3'-GTCAAGGGAAGTTAG-5' | 3 | +/− |

Underlined bases = Bases mutated from STAT 3 decoy

Sense and antisense strands were dissolved in Tris•EDTA (pH 8.0) at a concentration of 900-1,200 μM. Each sense-antisense pair was annealed by heating to 90° C. and decreasing the temperature by 5° C. increments every 15 min. After 3 h the reaction mixture was held at a base temperature of 4° C.

Earlier studies with transcription factor decoys have typically used a scrambled version of the decoy sequence as a control. Park et al., (1999) J. Biol. Chem. 274, 1573-1580; Sharma et al., (1996) Anticancer Res. 16, 589-596; Sharma et al., (1996) Anticancer Res. 16, 61-69; Sawa et al., (1997) Circulation 96 (Suppl.), II-280-II-284; Boccaccio et al., (1998) Nature 391, 285-288. and Akimoto et al. (1998) Exp. Eye Res. 67, 395-401. It has been suggested to design a control decoy with the greatest possible homology to the STAT 3 decoy, but with no STAT 3-specific DNA binding activity. For example, previous analysis of the c-fos promoter evaluated random mutations and reported their relative ability to induce SIF-binding activity. Wagner et al., (1990) EMBO J. 9, 4477-4484. Double or triple nucleotide mutants have been demonstrated to have variable degrees of binding to activated STAT 3. Analysis of the single nucleotide mutants revealed that several mutants appeared to have little or no binding to activated STAT 3.

The transcription factor signal transducer and activator of transcription 3 (STAT 3) is believed to be constitutively activated in a variety of cancers including squamous cell carcinoma of the head and neck (SCCHN). Previous investigations have demonstrated that activated STAT 3 contributes to a loss of growth control and transformation. The therapeutic potential of blocking STAT 3 in cancer cells may be determined by developing a transcription factor decoy to selectively abrogate activated STAT 3. A STAT 3 decoy may be composed of a 15-mer double-stranded oligonucleotide, which corresponds closely to the STAT 3 response element within the c-fos promoter. The STAT 3 decoy would bind specifically to activated STAT 3 and/or block binding of STAT 3 to a radiolabeled STAT 3 binding element. By contrast, a mutated version of the decoy that differed by only a single base pair would not bind the activated STAT 3 protein. One study reported that such treatment of head and neck cancer cells with the STAT 3 decoy inhibited proliferation and STAT 3-mediated gene expression, but did not decrease the proliferation of normal oral keratinocytes. Thus, disruption of activated STAT 3 by using a transcription factor decoy approach may play a role in the therapeutic strategy for cancers characterized by constitutive STAT 3 activation. Leong et al., PNAS 100(7):4138-4143 (2003).

STAT 3 decoy molecules appear to be safe and non-toxic that should be compatible for human administration. For example, an intramuscular administration of the STAT 3 decoy did not result in any local or consistent systemic abnormalities in monkeys. A single intramuscular injection in Cynomolgus monkeys did not result in the death of any animal or demonstrate evidence of systemic or organ-specific toxicity. Sen et al., Cancer Chemother Pharmacol (2009) 63:983-995. To date, in vitro studies have failed to demonstrate any toxicity of the STAT 3 decoy in normal mucosal epithelial cells after being treated with the STAT 3 decoy and there are no reports of any toxicity study using STAT 3 targeting agent in any in vivo model. Leong et al., Proc Natl Acad Sci USA 100:4138-4143.

The development of more effective prevention and treatment strategies for solid tumors may be limited by an incomplete understanding of the critical growth pathways that are activated in carcinogenesis. Signal transducers and activators of transcription (STAT) proteins have been linked to transformation and tumor progression. Several approaches have been used to block STAT 3 in cancer cells resulting in reduced proliferation and apoptosis. For example, blocking STAT 3 activation using a transcription factor decoy approach would decrease tumor growth and STAT 3 target gene expression in vivo. In a xenograft model of squamous cell carcinoma of the head and neck (SCCHN), daily administration of the STAT 3 decoy (25 µg) resulted in decreased tumor volumes, abrogation of STAT 3 activation, and decreased expression of STAT 3 target genes (VEGF, Bcl-xL, and cyclin D1) compared to treatment with a mutant control decoy. Blockade of STAT 3 with the STAT 3 decoy also induced apoptosis and decreased proliferation, an effect that was augmented when the STAT 3 decoy was combined with cisplatin, both in vitro and in vivo. These results suggest that a transcription factor decoy approach may be used to target STAT 3 in cancers that demonstrate increased STAT 3 activation including SCCHN. Xi et al., Oncogene (2005) 24, 970-979.

2. NF-kB Transcription Factor Decoy Molecules

The transcription factor nuclear factor-kappaB (NF-kappaB) may play a role in expression of many inflammatory genes responsible for the pathophysiology of sepsis-induced acute lung injury. It has been suggested that introduction of synthetic double-stranded oligodeoxynucleotides (ODNs) with consensus NF-kappaB sequence as transcription factor decoy can prevent acute lung injury with suppression of pulmonary expression of multiple genes involved in its pathological process in a cecal ligation and puncture septic mouse model. For example, NF-kappaB decoy ODNs may be introduced with the aid of the hemagglutinating virus of a Japan-envelope vector. Northern blot analysis may verify successful transfection of NF-kappaB decoy ODN. Pathological changes in lung tissue was strongly eliminated by the introduction of NF-kappaB decoy but not of scrambled ODN. Matsuda et al., "Nuclear factor-kappaB decoy oligodeoxynucleotides prevent acute lung injury in mice with cecal ligation and puncture-induced sepsis" Mol Pharmacol. 67:1018-1025 (2005).

Phosphorothioate double-stranded ODN sequences against NF-KB binding site and of scrambled ODN have been reported. Morishita et al., "In vivo transfection of cis element "decoy" against nuclear factor-κB binding site prevents myocardial infarction" Nature (Lond) Med 8:894-899 (1997). In one embodiment, a NF-KB transcription factor decoy molecules may comprise the sequences:

```
5'-CCTTGAAGGGATTTCCCTCC-3'        (SEQ ID NO: 35)
and

3'-GGAACTTCCCTAAAGGGAGG-5'.       (SEQ ID NO: 36)
```

Figure 22:
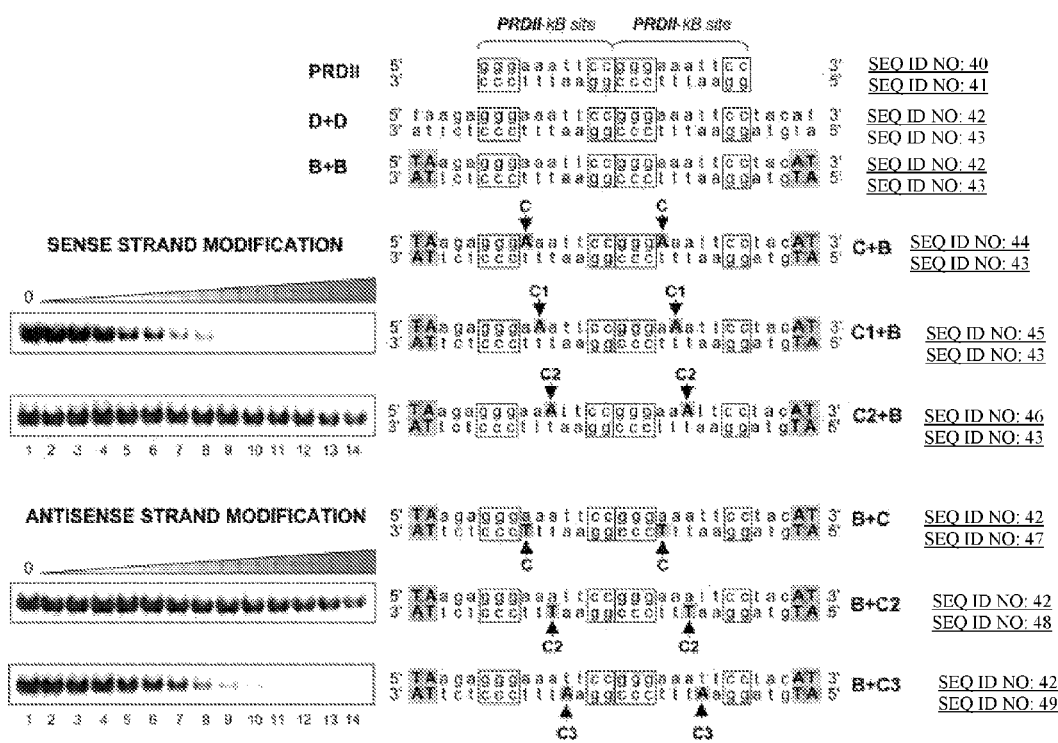
FIG. 22 illustrates an embodiment for the design of NF-kB transcription decoy molecules containing internal LNA substitutions only in one strand. Decoy molecules were derived from nucleic acid sequences of 30 bp, consisting of two PRDII KB sites in tandem (10 bp each, shown in braces), extended at the terminal ends with unrelated extra sequences of 5 nt (D+D, 30 bp) and modified by replacing the two terminal nucleotides with LNA monomers on both strands (B+B). Lower case, DNA monomers; bold upper case in grey, LNA bases. Besides the LNA end-block, additional LNA substitutions were introduced in the κB sequences at different positions other than C, tested in a previous study, of the sense (C1, C2) or of the antisense (C2, C3) strand, as indicated by the arrows. In replacing internal nucleotides with LNAs, those which establish base-specific contacts with NF-κB (in boxes) have been excluded. The ability of NF-κB to bind these molecules was assessed by gel shift competition experiments as described in Materials and Methods. Only the protein/probe complex is shown. Competitor concentrations in lanes 2-14 were 2.2, 3.3, 5.0, 7.5, 11.3, 16.9, 25.3, 38, 57, 85.8, 128.7, 193 and 289.6 nM.

Alternatively, NF-kB transcription decoy molecule may be custom designed. For example, a panel of decoy oligonucleotides may be modified to various extents and at various positions with LNA bases. Crinelli et al., "Design and characterization of decoy oligonucleotides containing locked nucleic acids" Nucleic Acids Res. 30:2435-2443 (2002). These oligonucleotides may comprise two κB sites, corresponding to the κB sequence contained in the PRDII domain of the human IFN-β promoter capped with unrelated extra sequences of 5 nt at both termini (Fig. (FIG. 1,1, D+D). See, FIG. 22. Insertion of at least two terminal LNA monomers, outside the κB motifs may be sufficient to confer appreciable protection against nuclease digestion, without interfering with transcription factor binding LNA substitutions positioned within the κB sites, by modifying nucleotides in both strands, further increased stability walkthrough a considerable reduction in NF-κB binding affinity was found. Other LNA substitutions in position C in the antisense strand reduced NF-κB binding affinity. Although it is not necessary to understand the mechanism of an invention, it is believed that this effect could be explained by the fact that LNA nucleotides perturb the sugar puckers of the flanking unmodified nucleotides, predominantly in the 3' direction, from a preferential S-type pucker in DNA duplexes to a mixture of N-type and S-type conformations. Nielsen et al., "Solution structure of an LNA hybridized to DNA: NMR study of the d(CTLGCTLTLCTLGC):d(GCA-GAAGCAG) duplex containing four locked nucleotides" Bioconjugate Chem., 11, 228-238 (2000); and Petersen et al., "The conformations of locked nucleic acids (LNA)" J. Mol. Recognit., 13:44-53 ((2000). It is further believed that this may represent a local rearrangement of the phosphate backbone geometry toward the A-type helix.

On the other hand, it has been reported that NF-?B recognizes the decameric consensus sequence 5'-GGGRN-NYYCC-3' (SEQ ID NO: 37) (N, any nucleotide; R, purine; Y, pyrimidine), where the transcription factor makes base-specific contacts mainly with the conserved G:C pairs at the ends of the site, lying in the major groove. Thus, the core of the site, in the minor groove, usually remains open. Reports suggest that PRDII to the High Mobility Group (HMG) I(Y) proteins specifically recognize and bind the central AT-rich sequence. Berkowitz et al., "The X-ray crystal structure of the NF-kB p50·p65 heterodimer bound to the interferon β-kB site" J. Biol. Chem., 277:24694-24700 (2002); and Escalante et al., "Structure of the NF-kB p50/p65 heterodimer bound to the PRDII DNA element from the interferon-β promoter" Structure 10:383-391 ((2002). As a consequence, the differences observed in NF-κB binding affinity for the C+B and B+C molecules could be due to the fact that the conformational modifications introduced by the LNAs in the sense strand (C+B) are mainly propagated to the AT-tract. Conversely, those introduced by the LNAs in antisense (B+C) presumably involve the GC-rich sequence, which is known to be particularly critical for interactions with NF-κB. Therefore, LNA decoys which are more efficiently recognized by NF-κB could be designed by a more convenient positioning of the internal LNA substitutions.

It has been reported that an NF-κB transcription factor decoy molecule may be useful in the treatment of cystic fibrosis because the transcription factor NF-kappaB may play a role in IL-8 expression. Decoy oligodeoxyribonucleotides (ODNs) have decreased the expression of IL-8 gene and concomitatnt secretion of IL-8 by cystic fibrosis cells infected by Pseudomonas aeruginosa. Gambari et al., "Decoy oligodeoxyribonucleotides and peptide nucleic acids-DNA chimeras targeting nuclear factor kappa-B: inhibition of IL-8 gene expression in cystic fibrosis cells infected with Pseudomonas aeruginosa" *Biochem Pharmacol.* 80(12):1887-1894 (2010).

Covalent binding of a synthetic DNA fragment with eukaryotic transcription factor NF-kappaB has been studied in lysates of human colon carcinoma HCT-116 cells. A 17-19 base pair nucleotide DNA duplex containing an NF-kappaB recognition site (kappaB-site) was used as a decoy molecule in which one of internucleotide phosphate groups was replaced by a chemically active trisubstituted pyrophosphate group. The construct was delivered in an intact tumor cell in a manner that penetrated through the plasma membrane. The activity of the decoy moleclue was verified because a subsequent treatment of the cells with TNF-alpha promoted partial translocation of the DNA reagent into the nucleus. Timchenko et al., "Modified DNA fragments specifically and irreversibly bind transcription factor NF-kappaB in lysates of human tumor cells" Biochemistry (Mose). 71(4): 454-460 (2006).

VIII. Kits

In another embodiment, the present invention contemplates kits for the practice of the methods of this invention.

The kits preferably include one or more containers containing various components to practice at least one embodiment of this invention. The kit can optionally include a first container comprising an ultrasound targeted microbubble population. The kit can optionally include a second container comprising a plurality of nucleic acids. The kit can optionally include a pharmaceutically acceptable excipient and/or a delivery vehicle (e.g., for clinical injections and the like). The reagents may be provided suspended in the excipient and/or delivery vehicle or may be provided as a separate component which can be later combined with the excipient and/or delivery vehicle. The kit may optionally contain additional therapeutics to be co-administered with the microbubble population. The nucleic acids in the second container may include but are not limited to oligonucleotide therapeutic molecules, siRNA, shRNA, RNAi, miRNA, antisense, transcription factor decoy molecules, deoxyribonucleic acid vectors, genes, and gene fragments. For example, the siRNA may be an EGFR siRNA. Alternatively, the transcription factor decoy molecule is an NF-kB transcription factor decoy molecule or a STAT 3 siRNA. The microbubble population in the first container may comprise a 7:14; 1 mixture of 1,2-distearoyl-sn-glycero-3-ethylphosphocholine (DSEPC), distearoylphosphatidyl-choline (DSPC), and PEG-40. The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the reagents in the methods of stably binding nucleic acids to a microbubble population. Further, the instructions may include providing for the ultrasonic delivery of the microbubble populations to a patient for the treatment of a disease and/or disorder. In particular the disease can include any one or more of the disorders described herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

REFERENCES

Aoi A, Watanabe Y, Mori S, Takahashi M, Vassaux G, Kodama T. Herpes simplex virus thymidine kinase-mediated suicide gene therapy using nano/microbubbles and ultrasound. Ultrasound Med Biot 2008; 34:425-434.

Becher H, Burns P N. Handbook of contrast echocardiography. Springer-Verlag; New York, USA, 2000.

Bekeredjian R, Chen S, Frenkel P A, Grayburn P A, Shohet R V. Ultrasound-targeted microbubble destruction can repeatedly direct highly specific plasmid expression to the heart. Circulation 2003; 108:1022-1026.

Bhattacharya A, Seshadri M, Oven S D, Tóth K, Vaughan M M, Rustum Y M. Tumor vascular maturation and improved drug delivery induced by methylselenocysteine leads to therapeutic synergy with anticancer drugs. Clin Cancer Res 2008; 14:3926-3932.

Chappell J C, Price R J. Therapeutic applications of acoustically active microspheres in the microcirculation. Microcirculation 2006; 13:57-70.

Chen S, Ding J H, Bekeredjian R, Yang B Z, Shohet R V, Johnston S A, Hohmeier H E, Newgard C B, Grayburn P A. Efficient gene delivery to pancreatic islets with ultrasonic microbubble destruction technology. PNAS 2006; 103:8469-8474.

Chen S, Ding J H, Yu C, Yang B, Wood D R, Grayburn P A. Reversal of streptozotocin-induced diabetes in rats by gene therapy with betacellulin and pancreatic duodenal homeobox-1. Gene Ther 2007; 14:1102-1110.

Chen S, Shimoda M, Wang M, Ding J, Noguchi H, Matsumoto S, Grayburn P A. Regeneration of pancreatic islets in vivo by ultrasound-targeted gene therapy. Gene Ther 2010; (in press).

Chen Z, Liang K, Liu J, Xi e M, Wang X, Lü Q, Zhang J, Fang L. Enhancement of survivin gene downregulation and cell apoptosis by a novel combination: liposome microbubbles and ultrasound exposure. Med Oncol 2009; 26:491-500.

Chen Z Y, Liang K, Xie M X, Wang X F, Lü Q, Zhang J. Induced apoptosis with ultrasound mediated microbubble destruction and shRNA targeting survivin in transplanted tumors. Adv Ther 2009; 26:99-106.

Christiansen J P, French B A, Klibanov A L, Kaul S, Lindner J R. Targeted tissue transfection with ultrasound destruction of plasmid-bearing cationic microbubbles. Ultrasound Med Biol 2003; 29:1759-1767.

de Jong N, Bouakaz Ayache, Frinking P. Basic acoustic properties of microbubbles. Echocardiography 2002; 19:229-240.

Fu K K, Rayner P A, Lam K N. Modification of the effects of continuous low dose rate irradiation by concurrent chemotherapy infusion. Int J Radiat Oncol Biol Phys 1984; 10:1473-1478.

Fujii H, Sun Z, Li S H, Wu J, Fazel S, Weisel R D, Rakowski H, Lindner J, Li R K. Ultrasound-targeted gene delivery induces angiogenesis after a myocardial infarction in mice. J Am Coll Cardiol Cardiovasc Imaging 2009; 2:869-879.

Gavrieli Y, Sherman Y, Ben-Sasson S A. Identification of programmed cell death in situ via specific labeling of nuclear DNA fragmentation. J Cell Bio 1992; 119:493-501.

Gomori, G. A rapid one-step trichrome stain. Am J Clin Pathol 1950; 20:661-663.

Greco A, Di Benedetto A, Howard C M, Kelly S, Dementieva Y, Miranda M, Brunetti A, Salvatore M, Claudio L, Sarkar D, Fisher P B, Claudio P P. Eradication of therapy-resistant human prostate tumors using an ultrasound-guided site-specific cancer terminator virus delivery approach. Molecular Therapy 2010; 18:295-306.

Hayashi S, Mizuno M, Yoshida J, Nakao A. Effect of sonoporation on cationic liposome-mediated IFNbeta gene therapy for metastatic hepatic tumors of murine colon cancer. Cancer Gene Ther 2009; 16:638-643.

Hershberger P A, Yu W D, Modzelewski R A, Rueger R M, Johnson C S, Trump D L. Calcitriol (1,25-dihydroxycholecalciferol) enhances paclitaxel antitumor activity in vitro and in vivo and accelerates paclitaxel-induced apoptosis. Clin Cancer Res 2001; 7:1043-1051

Jayaweera A R, Edwards N, Glasheen W P, Villanueva F S, Abbott R D, Kaul S. In-vivo myocardial kinetics of air-filled albumin microbubbles during myocardial contrast echocardiography: comparison with radiolabeled red blood cells. Circ Res 1994; 74:1157-1165.

Kaul S. Myocardial contrast echocardiography. A 25 year perspective. Circulation 2008; 118:291-308.

Li Y S, Davidson E, Reid C N, McHale A P. Optimising ultrasound-mediated gene transfer (sonoporation) in vitro and prolonged expression of a transgene in vivo: potential applications for gene therapy of cancer. Cancer Lett 2009; 273:62-69.

Maeda H, Tominaga K, Iwanaga K, Nagao F, Habu M, Tsujisawa T, Seta Y, Toyoshima K, Fukuda J, Nishihara T. Targeted drug delivery system for oral cancer therapy using sonoporation. J Oral Pathol Med 2009; 38:572-579.

Meijering B D, Juffermans L T, van Wamel A, Henning R H, Zuhom I S, Emmer M, Versteilen A M, Paulus W J, van Guist W H, Kooiman K, de Jong N, Musters R J, Deelman L E, Kamp O. Ultrasound and microbubble-targeted delivery of macromolecules is regulated by induction of endocytosis and pore formation. Circ Res 2009; 104:679-687. Nayak S, Herzog R W. Progress and prospects: immune responses to viral vectors. Gene Ther. 2010; 17:295-304.

Nie F, Xu H X, Lu M D, Wang Y, Tang Q. Anti-angiogenic gene therapy for hepatocellular carcinoma mediated by microbubble-enhanced ultrasound exposure: an in vivo experimental study. J Drug Target 2008; 16:389-395.

Parryl J J, Sharma V, Andrews R, Moros E G, Piwnica-Worms D, Rogers B E. PET imaging of heat-inducible suicide gene expression in mice bearing head and neck squamous cell carcinoma xenografts. Cancer Gene Therapy 2009; 16:161-170.

Price R J, Skyba D M, Kaul S, Skalak T C. Delivery of colloidal particles and red blood cells to tissue through microvessel ruptures created by targeted microbubble destruction with ultrasound. Circulation 1998; 98:1264-1267.

Rainov N G. A phase III clinical evaluation of herpes simplex virus type 1 thymidine kinase and ganciclovir gene therapy as an adjuvant to surgical resection and radiation in adults with previously untreated glioblastoma multiforme. Hum Gene Ther 2000; 11:2389-2401.

Rienhold H S, Visser J W. In vivo fluorescence of endothelial cell nuclei stained with the bis-benzamide H33342. Int J Microcirc Clin Exp 1983; 2:143-146.

Shand N, Weber F, Mariani L, Bernstein M, Gianella-Borradori A, Long Z, Sorensen A G, Barbier N. et al. A phase 1-2 clinical trial of gene therapy for recurrent glioblastoma multiforme by tumor transduction with the herpes simplex thymidine kinase gene followed by ganciclovir. Hum Gene Ther 1999; 10:2325-2335.

Thomas S M, Grandis J R. The current state of head and neck cancer gene therapy. Hum Gene Ther 2009; 8:2110-2120.

van Wamel A, Bouakaz A, Versluis M, de Jong N. Micromanipulation of endothelial cells:ultrasound-microbubble-cell interaction. Ultrasound Med Bio12004; 30:1255-1258.

Villanueva F S, Wagner W R. Ultrasound molecular imaging of cardiovascular disease. Nature Clin Prac Cardiovasc Med 2008; 5:26-32.

Villanueva F S. Ultrasound mediated destruction of DNA-loaded microbubbles for enhancement of cell-based therapies: new promise amidst a confluence of uncertainties? J Am Coll Cardiol Imaging 2009; 2:880-882.

Weller G, Villanueva F S, Klibanov A L, Wagner W R. Modulating targeted adhesion of an ultrasound contrast agent to dysfunctional endothelium. Ann Biomed Eng 2002; 30:1012-1019.

Weller G E, Wong M K, Modzelewski R A, Lu E, Klibanov A L, Wagner W R, Villanueva F S. Ultrasonic imaging of tumor angiogenesis using contrast microbubbles targeted via the tumor-binding peptide RRL. Cancer Res 2005; 65:533-539.

Zhao S, Ferrara K W, Dayton P A. Asymmetric oscillation of adherent targeted ultrasoundcontrast agents. Appl Phys Lett 2005; 87:134103-134106.

EXPERIMENTAL

Example I

Custom Microbubble Preparation And Confirmation of DNA Binding

DNA binding microbubbles were prepared from an approximate 7:14:1 mixture of 1,2-distearoyl-sn-glycero-3-ethylphosphocholine (DSEPC; approximately 625 micrograms) (Avanti Lipids, Alabaster, Ala.), distearoylphosphatidyl-choline (DSPC; approximately 1250 micrograms) (Avanti Lipids), and polyethylene glycol-40 (approximately 90 micrograms) (Sigma, St. Louis, Mo.) in PBS containing 1 mM EDTA.

This solution was placed in a glass vial, the head space was replaced with perfluorobutane gas, and the mixture was amalgamated to form perfluorobutane lipid encapsulated microbubbles.

Microbubbles were then centrifuged, washed 3 times with PBS/EDTA, and resuspended in PBS/EDTA, resulting in a microbubble concentration of $1-4 \times 10^9$/ml and diameter of 1.9-2.3 mm as measured by Coulter counting (Beckman Coulter, Brea, Calif.).

Plasmid DNA was attached by mixing plasmid (100 mg) and $1 \times 10^9$ microbubbles and briefly vortexing.

The following plasmid constructs were used:
  pEGFP-C1 (Clontech, Mountain View, Calif.), which contains the green fluorescent protein (GFP) gene driven by the CMV promoter;
  pCMV-Luc, in which the GFP gene in pEGFP-C1 was replaced with a firefly luciferase gene, and
  pCMV-TK, in which the GFP gene in pEGFP-C1 was replaced with the herpes simplex virus-1 TK gene.

DNA binding to the microbubbles was confirmed by serial washing at different time points up to 8 hours after DNA attachment and recovering DNA from both bound and unbound (wash) fractions using chloroform/isoamyl alcohol (24:1) fractionation to burst microbubbles and remove lipid components. Equivalent sample volumes were then analyzed for DNA content by standard agarose gel electrophoresis followed by ethidium bromide staining.

Figure 7:
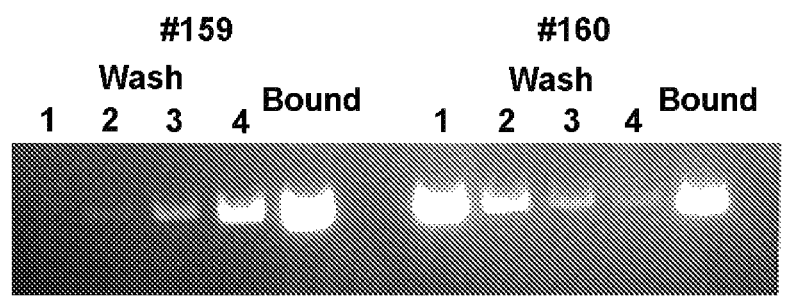
FIG. 7: Representative data comparing the relative DNA binding capability of cationic microbubble formulation #159 versus cationic microbubble formulation #160 (see Example I).
Figure 8:
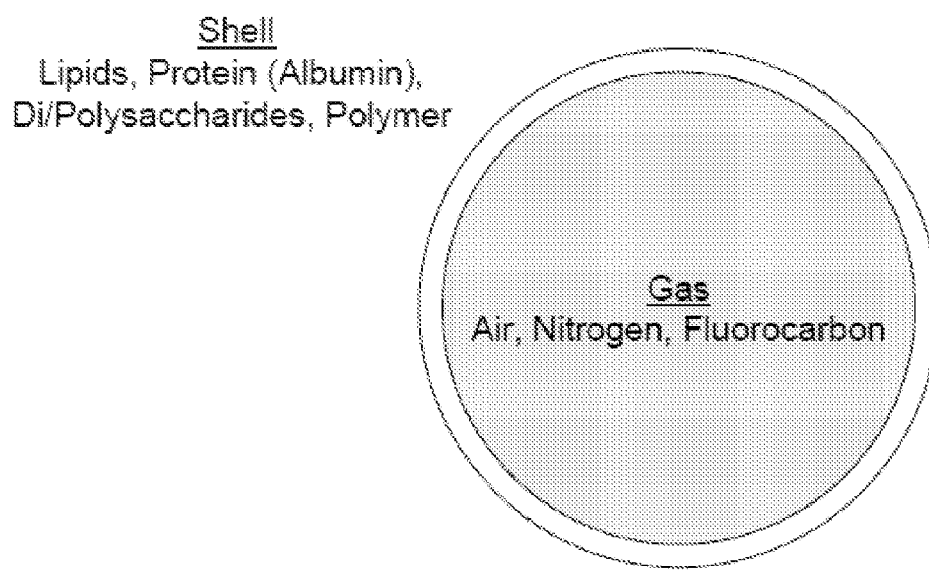
FIG. 8 illustrates one embodiment of a microbubble comprising a shell with components including but not limited to Lipids, Protein (Albumin), Di/Polysaccharides, and/or Polymers.
Figure 9:
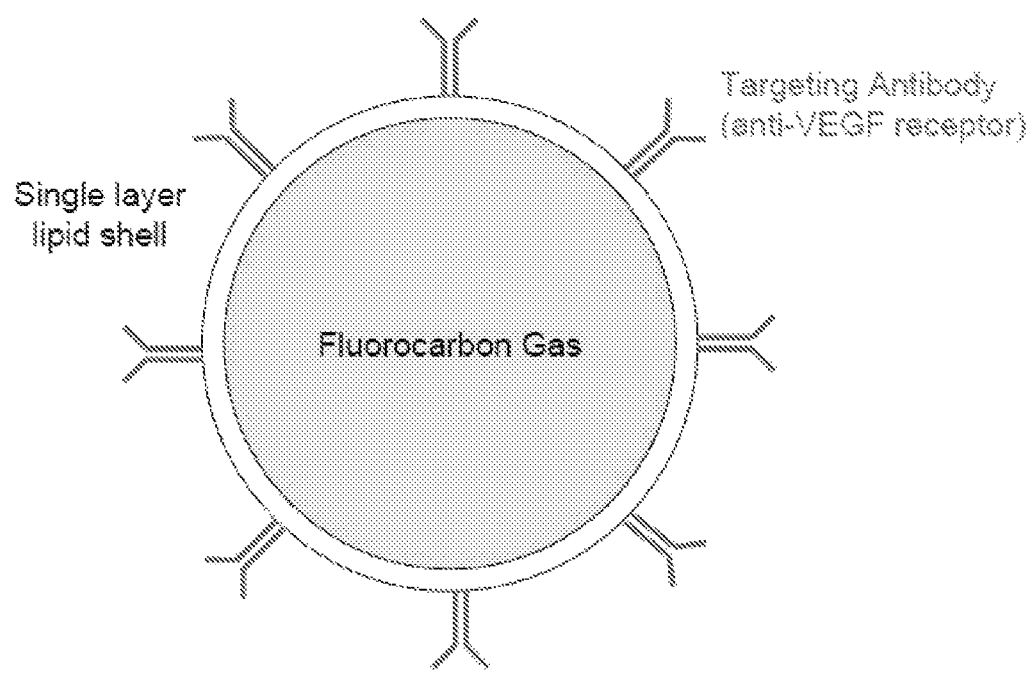
FIG. 9 presents one embodiment of a single layered microbubble shell configured with targeted antibodies.
Figure 10:
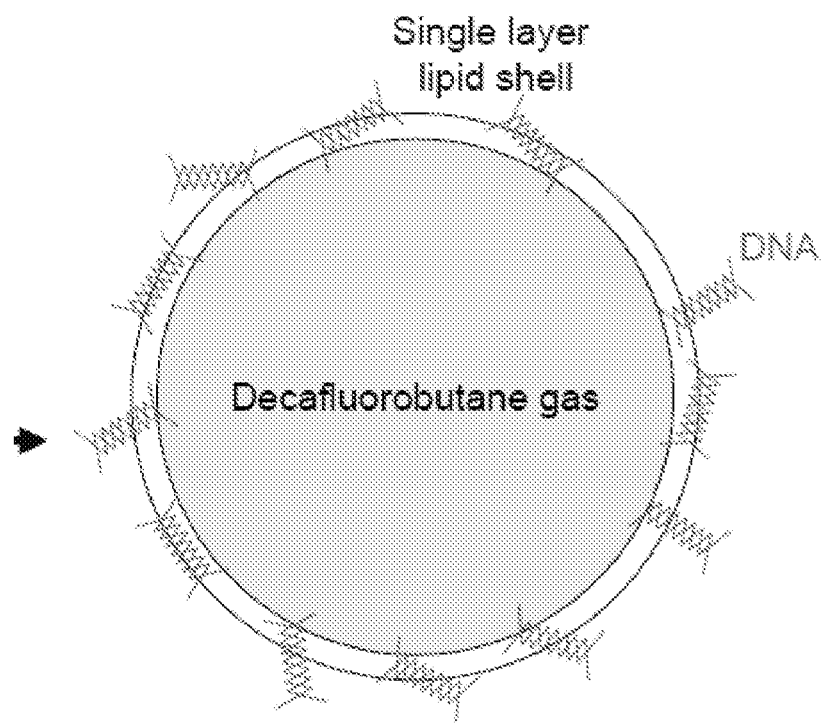
FIG. 10 presents one embodiment of a single layered microbubble shell configured with nucleic acids (e.g., DNA).
Figure 11:
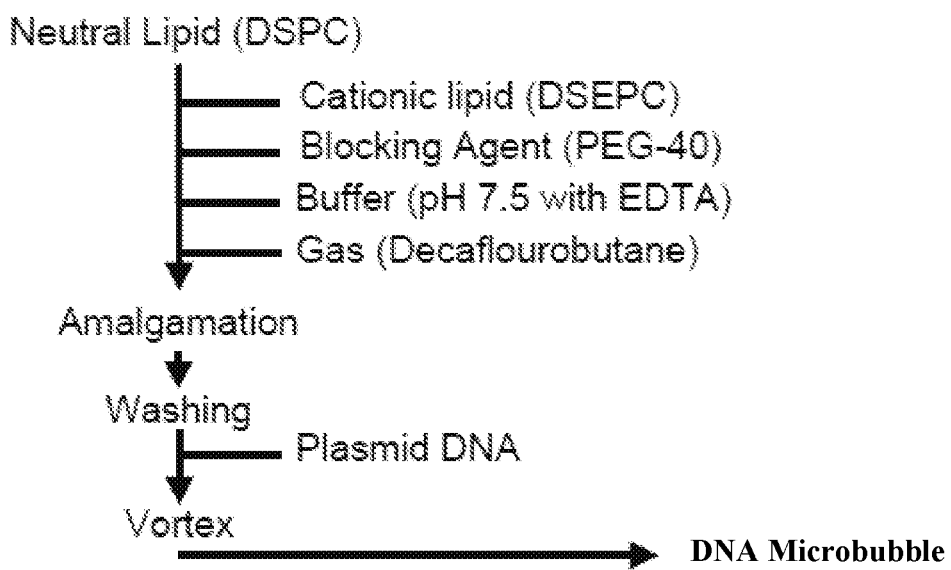
FIG. 11 presents one embodiment of a formulation scheme to create the microbubble of FIG. 10.

Two modifications were also compared. Recipe #159 used DSEPC to provide a cationic charge, whereas Recipe #160 used DOTAP to impart a cationic charge. The data illustrates a difference in binding between recipe #159 (which was modified only slightly to yield our resulting final MB) and recipe #160, which was much less successful at binding plasmid DNA. See, FIG. 7. Specifically, more DNA washes off from #160 microbubbles, indicating less binding capability, as compared to #159 microbubbles.

Example II siRNA Binding Efficiency to Microbubbles

This example demonstrates efficient RNA binding to a microbubble population using agarose gel electrophoresis.

siRNA-binding microbubbles were prepared from a mixture of 5 µg/ml siRNA, 625 µg/ml 1,2-distearoyl-sn-glycero-3-phosphocholine, 282 µg/ml 1,2-distearoyl-sn-glycero-3-ethylphosphocholine, 6.5 µg/ml 1,2-distearoyl-sn-glycero-3-phospho-(1'-rac-glycerol), and 72 µg/ml polyethylene glycol-40 in PBS containing 1 mM EDTA in accordance with Example I.

Figure 12:
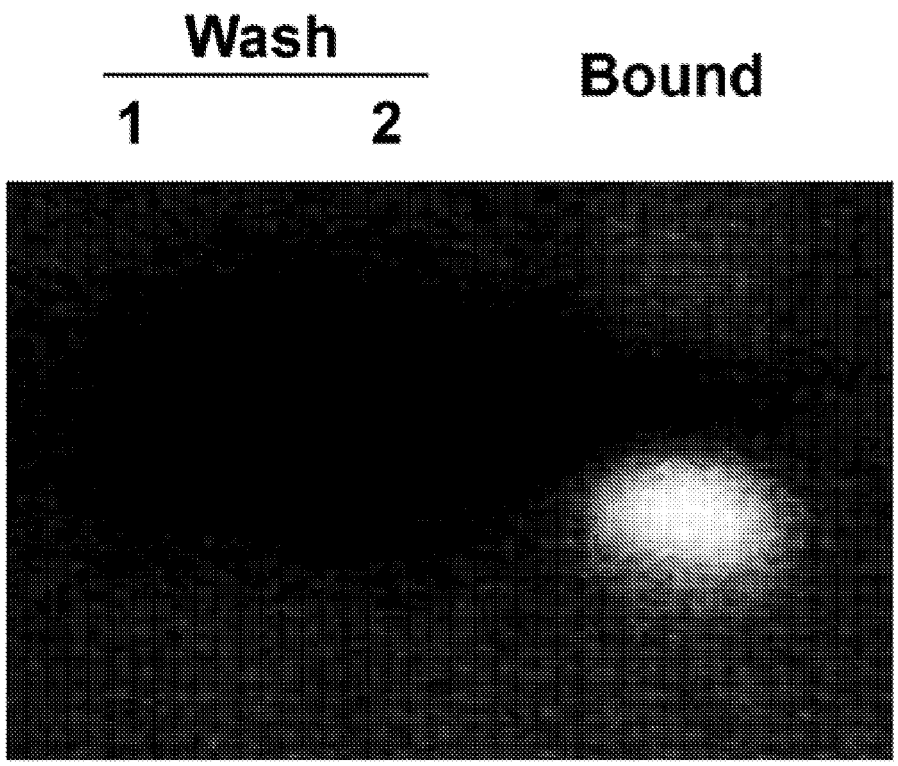
FIG. 12 presents exemplary data showing the recovery of siRNA after stable binding to a microbubble population. Lanes 1 and 2: Wash recovery assay. Lane 3: Recovery of bound siRNA following destruction of the microbubble population

Microbubbles loaded with siRNA specific to GFP were washed 2 times to remove unbound nucleic acid (wash lanes 1-2). Microbubbles were destroyed and bound RNA was recovered ("Bound", lane 3). The labeling data show the recovery of a significant amount of siRNA. See, FIG. 12.

Example III

Quantitation Estimation of Microbubble siRNA Binding Efficiency

This example estimated the bound quantity of siRNA binding to a microbubble population using agarose gel electrophoresis by comparison to siRNA concentration controls samples.

Figure 13:
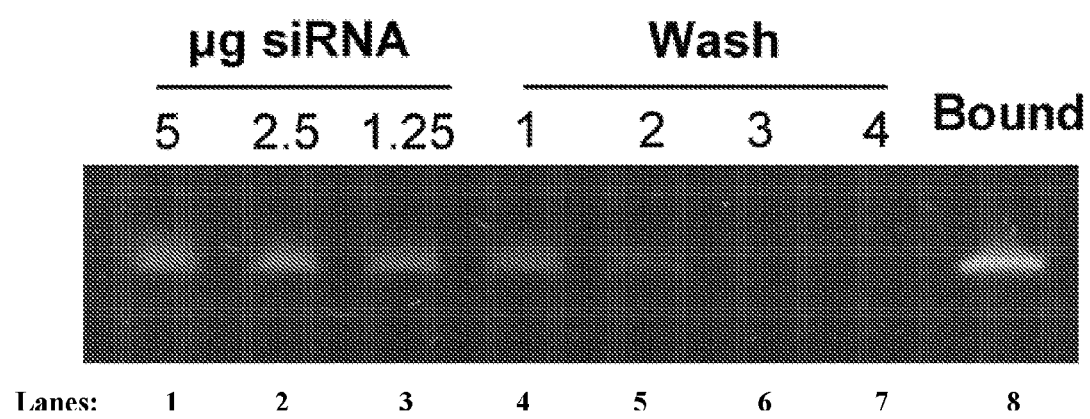
FIG. 13 presents exemplary data showing an estimated quantitation of bound siRNA to a microbubble population. Lanes 1-3: siRNA control samples. Lanes: 4-7: siRNA collected during consecutive washes. Lanes 8: siRNA present following destruction of the microbubble population.

RNA binding microbubbles were prepared from a mixture of 5 µg/ml siRNA, 625 µg/ml 1,2-distearoyl-sn-glycero-3-phosphocholine, 282 µg/ml 1,2-distearoyl-sn-glycero-3-ethylphosphocholine, 6.5 µg/ml 1,2-distearoyl-sn-glycero-3-phospho-(1'-rac-glycerol), and 72 µg/ml polyethylene glycol-40 in PBS containing 1 mM EDTA Microbubbles loaded with Silencer Select (Ambion) siRNA specific to EGFR were washed 4 consecutive times to remove unbound nucleic acid (wash lanes 4-7). Microbubbles were destroyed and bound RNA was recovered ("Bound", lane 8). Lanes 1-3 were loaded with 1.25-5 µg RNA as loading controls. The data show that the bound siRNA to the microbubble was in excess of 5 µg. See, FIG. 13.

Example IV

Inhibition of Tumor Growth with siRNA-Microbubbles

This example shows reduced growth of murine tumors after intravenous injection of Silencer Select anti-EGFR siRNA loaded microbubbles.

Murine tumors were treated with microbubbles bound with anti-EGFR siRNA in the presence and absence of ultrasound mediated destruction (UMTD). Control tumors were treated with empty microbubbles and ultrasound mediated destruction. Microbubble injections and UMTD was performed on day 0 and again on day 3 or 4 for a total of two injections per mouse. Best fit lines were calculated from all data points in each group assuming an exponential growth curve.

Figure 14:
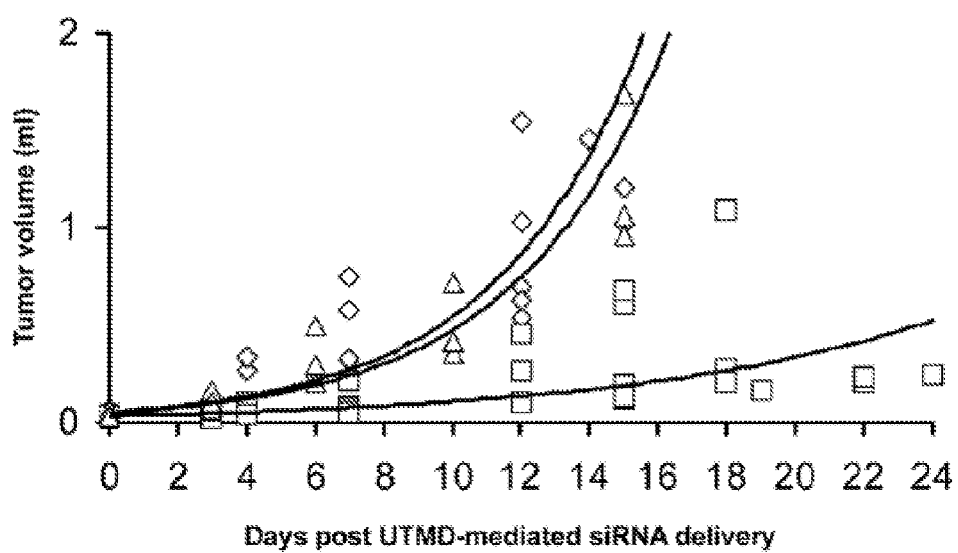
FIG. 14 presents exemplary data showing reduced in vivo murine tumor growth using microbubbles (MB) bound to siRNA Squares: siRNA-MB with UMTD; Triangles: siRNA-MB without UMTD; Diamonds: MB's alone+ UMTD.

The data showed that tumor cell doubling times of these groups are as follows:
siRNA with UMTD (squares): 5.29±2.01 days
siRNA without UMTD (triangles): 2.01±0.13 days
empty MB+UMTD (diamonds): 2.14±0.20 days
The differences between the treatment and control groups are statistically significant (p=0.002 to 0.03). See, FIG. 14 and FIG. 15.

Example V

Inhibition of Tumor Growth with Transgene-Microbubbles

A first study employed nine (9) mice to determine the extent and location of UMTD-mediated transduction using microbubbles loaded with pCMV-Luc (luciferase, n=6) and pEGFP-C1 (GFP n=3), respectively. Eight (8) control mice received the identical microbubble injection (luciferase n=5 and GFP n=3), but no ultrasound. These seventeen (17) mice were euthanized 3 days later and the tumors were harvested.

A second study employed five (5) mice that were administered intravenous microbubbles loaded with pCMV-TK vectors and delivered to the tumor site using UMTD. Six (6) control mice were administered intravenous microbubbles loaded with pEGFP-C1 vectors and delivered using UMTD. Both groups were administered GCV (80 mg/kg) IP daily for the duration of the protocol, commencing 3 days after UMTD. Tumor volume was serially measured and mice were euthanized and the tumor was harvested when tumor volume reached 2 ml. A separate group of 4 mice (n=2 TK, n=2 GFP) were euthanized 3 days after microbubble delivery and UMTD treatment, but prior to GCV treatment, to evaluate tumor morphology early after UMTD.

Example VI

DNAse I Protection Assay

To determine whether plasmid DNA on the surface of a microbubble might be protected from DNAses present in the circulation, DNA-loaded microbubbles prepared as above with 50 mg DNA resuspended in 1 ml reaction buffer containing 10 mM Tris 7.6 and 2.5 mM $MgCl_2$ and challenged with a range of DNase I concentrations from 0.0003 units/ml to 1 unit/ml (New England Biolabs, Ipswich, Mass.); as a positive control, 50 µg DNA was challenged under the same conditions in the absence of microbubbles.

Example VII

Luciferase Assays

Luciferase expression was quantified using the Promega Luciferase Assay System (Promega, Madison, Wis.). Briefly, tissue samples were homogenized, protein content was estimated by Bradford assay, and luciferase activity was detected using a luminometer with a 20 second sampling time. Raw luciferase activity was subtracted from background readings obtained from resuspension buffer alone and expressed as RLU/min/mg of protein.

Example VIII

Immunofluorescent And Histochemical Staining

Immunofluorescent staining was used to confirm transduction of GFP and identification of vascular or lymphatic endothelial cells. Tumor samples were frozen in OCT embedding media, sectioned, fixed with 10% formalin, blocked, washed, and incubated with primary antibody for GFP (Invitrogen, Carlsbad, Calif.); the endothelial markers von Willebrand factor (vWF) (Dako, Carpinteria, Calif.) or biotinylated Griffonia Simplicifolia Lectin I (Vector Labs, Burlingame, Calif.); the macrophage marker CD68 (Abcam, Cambridge, Mass.); or the lymphatic marker LYVE1 (Abcam, Cambridge, Mass.). After washing, slides were incubated with either secondary anti-rabbit FITC conjugate (Molecular Probes, Eugene, Oreg.) or Strepavidin-FITC conjugate (Sigma, St Louis, Mo.), washed, counterstained with DAPI, coverslips were added and visualized on an Olympus IX81 microscope (Center Valley, Pa.) interfaced with digital CCD camera (Olympus DP71). TUNEL analysis was performed using the ApopTag kit according to vendor protocols (Millipore, Billerica, Mass.) to identify apoptotic cells (Gavrieli et al. 1992).

Example XI

Structural Characterization of Tumors

Standard hematoxylin and eosin (H&E) staining in accordance with Example VII was performed on 6 mm tumor sections. During initial H&E staining, treated tumors were noted to have scattered areas of cell dropout. To standardize definitions and further quantify this phenomenon, we defined these acellular areas as having maximum diameters greater than 25 mm and a short axis to long axis ratio of less than 1:4, to distinguish them from small cracks due to tissue processing. The acellular zones defined as such were counted, the total area of each cross section was determined, and the number of acellular zones was calculated as zones per mm2. Formalin fixed sections were stained with 0.2% Oil Red 0 (Sigma, St Louis, Mo.) or Gomori Trichrome (Protocol, Kalamazoo, Mich.), to detect adipose cells or fibrosis, respectively, in the cell dropout areas (Gomori 1950). To determine if areas of cell dropout were connected to the systemic circulation, the intravascular stain Hoescht 33342 (8 μg/g) was injected intravenously 6 minutes before euthanasia and tissue harvest (Reinhold and Visser 1983).

Example X

Mouse Tumor Model

The animal protocols were approved by the University of Pittsburgh Institutional Animal Care and Use Committee and conformed to the PHS Policy on the Humane Care and Use of Laboratory Animals. Mouse squamous cell tumors were induced as previously described (Fu et al. 1984). Mouse squamous cell carcinoma cells were cultured and passed no more than 4 times in vitro prior to use. C3H/NeJ mice received subcutaneous injection of 5×105 carcinoma cells over the dorsal surface of the thoracic/lumbar spine under isofluorane anesthesia. In this model tumors typically grow to 0.5 ml by 10-12 days after injection. On the day of gene therapy, animals were re-anesthetized, and the jugular vein was cannulated. After injection, mice were recovered and administered 0.6 mg/kg IP buprenorphine daily for three days post surgery.

Example XI

Serial Measurement of Tumor Volume

The mice were anesthetized with isofluorane and positioned for imaging. Cross sectional ultrasound images (14 MHz, Sequoia, Siemens Corp, Mountain View, Calif.) of the tumor were digitally acquired by fixing the transducer to a microstage manipulator with millimeter calibrations and moving the transducer at 1 mm increments along the long axis of the tumor. Areas from each 1 mm thick cross section were planimetered and summed to yield the total tumor volume. This approach was chosen over conventional caliper measurements as they do not assume an elliptical tumor shape and the imaging can visualize full tumor thickness below the skin.

Example XII

Ultrasound Transduction Treatment Protocol

Daily measurement of tumor volume was initiated 7 days after injection of the tumor cells and UMTD commenced when tumor volume was 0.1-0.15 ml by ultrasound measurement. Microbubbles (1 ml) were infused into the jugular vein over 20 minutes in conjunction with ultrasound delivery to the tumor over 30 minutes. Ultrasound imaging was combined with UMTD using a two-transducer system to perform concurrent high frequency, low power two-dimensional perfusion imaging and lower frequency, high power microbubble destruction. Specifically, microbubble perfusion of the tumor was visualized in real time using ultrasound (7 MHz, Contrast Pulse Sequencing, Sequoia, Siemens Corp, Mountain View, Calif.). at a low acoustic power (Mechanical Index 0.4) to minimize microbubble destruction Upon visualization of microbubbles within the tumor, microbubbles were burst using an orthogonally placed ultrasound transducer (S3 probe, Sonos 7500, Philips, Andover, Mass.) delivering ultrasound at 1.3 MHz and a Mechanical Index of 1.6, with the 7 MHz imaging transducer confirming successful microbubble destruction. Destructive ultrasound bursts were repeated each time that microbubble replenishment of the tumor was visualized. The interval between destructive ultrasound bursts was adjusted to allow full microbubble reperfusion of the tumor prior to the next burst cycle. The number of destructive ultrasound bursts was adjusted to the minimum number required to destroy most bubbles in the tumor as visualized during concurrent low MI imaging. Thereafter, the venous cannula was removed and the mice were recovered.

Example XIII

Reduction in Tumor Growth with UTMB Delivery of EGFR siRNA

EGFR siRNA Constructs
The following 2 siRNA constructs will be used:
 (1) Mouse EGFR silencer select predesigned siRNA (ID# s65373) (Ambion, Foster City, Calif.). Sequence:

Sense (5' to 3'):

GGAGGGACAUCGUCCAAAATT; (SEQ ID NO: 38)

AntiSense (5' to 3'):

UUUUGGACGAUGUCCCUCCAC (SEQ ID NO: 39)

(2) Silencer Select negative control siRNA #1 (Cat# AM4635) (Ambion, Foster City, Calif.). Sequence: Proprietary. The siRNAs have been screened by Ambion for possible immunoactive effects using sequence analysis and microarray (Ambion).

Mouse Tumor Model

All animal protocols were approved by the University of Pittsburgh Institutional Animal Care and Use Committee and conformed to the PHS Policy on the Humane Care and Use of Laboratory Animals. Mouse squamous cell tumors were induced as previously described (Carson 2011, Fu et al. 1984). Briefly, mouse squamous cell carcinoma cells were cultured in vitro and $5 \times 10^5$ cells were subcutaneously injected into the dorsal surface of the thoracic/lumbar spine under general anesthesia. To facilitate multiple microbubble injections and UMTD treatments, mice were reanesthetized, and an indwelling catheter made of PE-10 tubing was placed in the jugular vein, secured, and threaded subcutaneously around the mouse to emerge on the dorsal surface of the mouse, near the base of the skull along the midline. After each microbubble injection and ultrasound treatment, mice were recovered and administered 0.6 mg/kg IP buprenorphine daily for three days post surgery.

Serial Measurements of Tumor Volume

The mice were anesthetized with isofluorane and positioned for high resolution 3D imaging on the first day of treatment and every 2-4 days after. 3D scanning of tumors was obtained at using the automated 3D scan mode of the Visualsonics Vevo 2100 system at 21 MHz, with a 0.197 mm step size. Tumor cross sections were outlined from these data manually and volumes were calculated from 3D reconstructions of these areas. This method of volume estimation is similar to that used in (Carson et al), although with improved resolution and volume detection software. This technique was chosen over conventional caliper measurements as it does not assume an elliptical tumor shape, accurately detects the depth of the tumor, and can detect and measure tumors as small as 0.02 ml.

siRNA Injection and UMTD Treatment

Tumors were measured daily 7 days after Squamous cell carcinoma injection treatment was initiated when tumor volumes reached 0.02-0.04 ml. siRNA (5 ug) loaded microbubbles ($\sim 7 \times 10^8$) were suspended in 0.4 ml PBS and infused through the indwelling catheter into the jugular vein over a 20 minute period. Destructive ultrasound was delivered to tumors over a period of 30 minutes. As described in Carson 2011, imaging and UMTD were combined using a two-transducer system. Briefly, imaging was performed at 7 MHz, using Contrast Pulse Sequencing (Sequoia, Siemens Corp, Mountain View, Calif.) and UMTD was delivered at 1.3 MHz with a mechanical index of 1.6 (S3 probe, Sonos 7500, Philips, Andover, Mass.).

Experimental Groups

Six mice were used to detect UMTD-mediated siRNA knockdown of EGFR in murine tumors after delivery of microbubbles loaded with anti-EGFR siRNA (n=3) or negative control siRNA (n=3). Mice were euthanized 4 days after microbubble/siRNA injection and tumor was harvested for immunofluorescent and western blot analysis. Therapeutic studies were performed after two injections of siRNA loaded microbubbles and UMTD treatments (performed on days 1 and day 4 or 5). Seven mice were injected with intravenous microbubbles loaded with anti-EGFR siRNA, five mice were injected with empty microbubbles, and six mice were injected with microbubbles loaded with control siRNA. Tumor volumes were serially measured on each mouse and mice were euthanized and the tumor was harvested when tumor volume exceeded 1 ml, if there was evidence of ulceration, or after 4 weeks.

Western Blot

Tumor tissue was homogenized in RadioImmunoPrecipitation Assay (RIPA) buffer, and protein was quantified using a Bradford assay (Sigma, St. Louis, Mo.). Equal levels of protein was then electrophoresed on either a 7.5% acrylamide (for EGFR) or a 12% acrylamide gel (for B-actin). Protein was then transferred to nitrocellulose membrane and subjected to western blot using either purified mouse anti-EGFR antibody (BD Biosciences) or mouse B-actin antibody and a anti-mouse HRP secondary antibody (Sigma).

Immuno Fluorescence

Tumor tissue was frozen in optimal cutting temperature media and sectioned at 5 microns for immunofluorescent staining to detect EGFR in tumor tissue. Slides were blocked, washed and incubated with primary antibody for EGFR (BD Biosystems). After washing, slides were incubated with secondary anti-mouse FITC conjugate (Sigma), and counterstained with DAPI (Sigma, Saint Louis, Mo.). All slides were visualized on an Olympus IX81 microscope (Center Valley, Pa., USA) interfaced with digital CCD camera (Olympus DP71).

Statistical Methods

All data are expressed as mean±standard deviation. To calculate tumor doubling time for individual tumors, tumor volume measurements (y) were plotted as a function of time (t) and fit to the exponential function $y=X_0 \cdot e^{kt}$, where $X_0$ is the tumor volume at time 0. Doubling time (Dt) was calculated as $Dt=\ln 2/k$. Doubling times were then compared using a Kruskal-Wallis combined test and confirmed with a pairwise follow-up test using Dunn's method. All statistical tests were performed using Sigma-Stat software (Aspire Software, Ashburn, Va.). Tumor volume measurements were also used to create a Kaplan-Meier curve that reports days to critical volume for each individual mouse. 0.3 ml was chosen as a critical volume as this is the smallest volume of a mouse that developed an ulcerated tumor. As mice with ulcerated tumors must be euthanized for humane reasons, this is the latest reliable measurement available for all mice. The time to critical volume between groups was compared using the log-rank stat, followed by a Bonferroni-corrected pair wise analysis. All statistical tests were performed using Sigma-Stat software (Aspire Software, Ashburn, Va.).

Example XIV

Statistical Methods

Some data herein are expressed as mean±standard deviation. Means were compared using 2-tailed Student's t-test (unpaired), with significance defined as $p<0.05$. To calculate tumor doubling time for individual tumors, tumor volume measurements (y) were plotted as a function of time (t) and fit to the exponential function $y=X_0 \cdot e^{kt}$, where $X_0$ is the tumor volume at time 0. Doubling time (Dt) was calculated as $Dt=\ln 2/k$. Group sizes were determined by a priori power analysis using doubling times (~3 days) and standard deviations (~10%) from preliminary studies. Using these estimates, group sizes of at least 5 are appropriate to detect a 20% or more difference in tumor doubling time with a power of ~90%.

The invention claimed is:

1. A method for treating a cancer disease comprising,
   a) providing:
      i) a patient comprising a solid tumor, said tumor having a cancer cell;
      ii) a microbubble population stably binding a plurality of nucleic acids; and
      iii) an ultrasound device comprising a low power ultrasound transducer and a high power ultrasound transducer;
   b) administering said microbubble population systemically to said patient;
   c) imaging said microbubble population and said cancer cell with said low power ultrasound transducer; and
   d) transfecting said imaged cancer cell with said plurality of nucleic acids by bursting said systemic microbubble population with said high power transducer, wherein the growth of said cancer cell is reduced.

2. The method of claim 1, wherein said cancer cell expresses said plurality of nucleic acids.

3. The method of claim 1, wherein said nucleic acids are selected from the group consisting of oligonucleotide therapeutic molecules, siRNA, shRNA, RNAi, miRNA, antisense, transcription factor decoy molecules, deoxyribonucleic acid vectors and genes.

4. The method of claim 3, wherein said siRNA is an EGFR siRNA.

5. The method of claim 3, wherein said transcription factor decoy molecule is an NF-kB transcription factor decoy molecule.

6. The method of claim 3, wherein said deoxyribonucleic acid vector comprises a cytomegalovirus promoter sequence and a thymidine kinase sequence (pCMV-TK).

7. The method of claim 1, wherein said low power ultrasound transducer is configured orthogonally to said high power ultrasound transducer.

8. The method of claim 1, wherein said cancer cell is a carcinoma cell.

9. The method of claim 1, wherein said cancer cell is a colorectal cancer cell.

10. The method of claim 8, wherein said carcinoma cell is selected from the group consisting of squamous cell carcinoma cell, prostate carcinoma cell, breast carcinoma cell, lung carcinoma cell, pancreas carcinoma cell, ovarian carcinoma cell, head carcinoma cell and neck carcinoma cell.

11. The method of claim 1, wherein said stably bound nucleic acids are protected from cleavage by a nuclease.

12. The method of claim 1, wherein said stably bound nucleic acids are protected from dissociation by repetitive washings.

* * * * *

UNITED STATES PATENT AND TRADEMARK OFFICE
CERTIFICATE OF CORRECTION

PATENT NO.         : 9,844,504 B2
APPLICATION NO.    : 13/640954
DATED              : December 19, 2017
INVENTOR(S)        : Villanueva et al.

It is certified that error appears in the above-identified patent and that said Letters Patent is hereby corrected as shown below:

In the Specification

Column 1, Line 15, under the heading DESCRIPTION and before the heading FIELD OF INVENTION, please insert the following:
--GOVERNMENT SUPPORT
This invention was made with government support under Grant No. RO1HL077534-01 awarded by the National Institutes of Health. The government has certain rights in the invention.--

Signed and Sealed this
Tenth Day of July, 2018

Andrei Iancu
*Director of the United States Patent and Trademark Office*

SEQUENCE LISTING

<160> NUMBER OF SEQ ID NOS: 49

<210> SEQ ID NO 1
<211> LENGTH: 6
<212> TYPE: DNA
<213> ORGANISM: Artificial Sequence
<220> FEATURE:
<223> OTHER INFORMATION: Synthetic

<400> SEQUENCE: 1 gggcgg                                                                    6

<210> SEQ ID NO 2
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: The residue in this position can be either "G"
      or "C"

<400> SEQUENCE: 2 tgantca                                                                   7

<210> SEQ ID NO 3
<211> LENGTH: 10
<212> TYPE: DNA
<213> ORGANISM: Artificial Sequence
<220> FEATURE:
<223> OTHER INFORMATION: Synthetic

<400> SEQUENCE: 3
attgcgcaat                                                               10

<210> SEQ ID NO 4
<211> LENGTH: 5
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t

<400> SEQUENCE: 4 ngaan                                                                     5

<210> SEQ ID NO 5
<211> LENGTH: 8
<212> TYPE: DNA
<213> ORGANISM: Artificial Sequence
<220> FEATURE:
<223> OTHER INFORMATION: Synthetic

<400> SEQUENCE: 5 tgacgtca                                                                  8

<210> SEQ ID NO 6
<211> LENGTH: 6
<212> TYPE: DNA

```
<213> ORGANISM: Artificial Sequence
<220> FEATURE:
<223> OTHER INFORMATION: Synthetic

<400> SEQUENCE: 6 cacgtg                                                                    6

<210> SEQ ID NO 7
<211> LENGTH: 8
<212> TYPE: DNA
<213> ORGANISM: Artificial Sequence
<220> FEATURE:
<223> OTHER INFORMATION: Synthetic

<400> SEQUENCE: 7 atgcaaat                                                                  8

<210> SEQ ID NO 8
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t

<400> SEQUENCE: 8
ttggcnnnnn gccaa                                                         15

<210> SEQ ID NO 9
<211> LENGTH: 15
<212> TYPE: DNA
<213> ORGANISM: Artificial Sequence
<220> FEATURE:
<223> OTHER INFORMATION: Synthetic

<400> SEQUENCE: 9
catttcccgt aaatc                                                         15

<210> SEQ ID NO 10
<211> LENGTH: 15
<212> TYPE: DNA
<213> ORGANISM: Artificial Sequence
<220> FEATURE:
<223> OTHER INFORMATION: Synthetic

<400> SEQUENCE: 10
catttacggg aaatg                                                         15

<210> SEQ ID NO 11
<211> LENGTH: 14
<212> TYPE: DNA
<213> ORGANISM: Artificial Sequence
<220> FEATURE:
<223> OTHER INFORMATION: Synthetic

<400> SEQUENCE: 11
catttcctta aatc                                                          14

<210> SEQ ID NO 12
<211> LENGTH: 15
<212> TYPE: DNA
<213> ORGANISM: Artificial Sequence
<220> FEATURE:
<223> OTHER INFORMATION: Synthetic
```

```
<400> SEQUENCE: 12
gatttaaggg aaatg                                                    15

<210> SEQ ID NO 13
<211> LENGTH: 15
<212> TYPE: DNA
<213> ORGANISM: Artificial Sequence
<220> FEATURE:
<223> OTHER INFORMATION: Synthetic

<400> SEQUENCE: 13
cagttccctt aaatc                                                    15

<210> SEQ ID NO 14
<211> LENGTH: 15
<212> TYPE: DNA
<213> ORGANISM: Artificial Sequence
<220> FEATURE:
<223> OTHER INFORMATION: Synthetic

<400> SEQUENCE: 14
gatttaaggg aactg                                                    15

<210> SEQ ID NO 15
<211> LENGTH: 15
<212> TYPE: DNA
<213> ORGANISM: Artificial Sequence
<220> FEATURE:
<223> OTHER INFORMATION: Synthetic

<400> SEQUENCE: 15
cagttcccgt aaatc                                                    15

<210> SEQ ID NO 16
<211> LENGTH: 15
<212> TYPE: DNA
<213> ORGANISM: Artificial Sequence
<220> FEATURE:
<223> OTHER INFORMATION: Synthetic

<400> SEQUENCE: 16
gatttacggg aactg                                                    15

<210> SEQ ID NO 17
<211> LENGTH: 15
<212> TYPE: DNA
<213> ORGANISM: Artificial Sequence
<220> FEATURE:
<223> OTHER INFORMATION: Synthetic

<400> SEQUENCE: 17
catttcacgt aaatc                                                    15

<210> SEQ ID NO 18
<211> LENGTH: 15
<212> TYPE: DNA
<213> ORGANISM: Artificial Sequence
<220> FEATURE:
<223> OTHER INFORMATION: Synthetic

<400> SEQUENCE: 18
gatttacgtg aaatg                                                    15

<210> SEQ ID NO 19
```

```
<211> LENGTH: 15
<212> TYPE: DNA
<213> ORGANISM: Artificial Sequence
<220> FEATURE:
<223> OTHER INFORMATION: Synthetic

<400> SEQUENCE: 19
catttccctt aaatc                                                    15

<210> SEQ ID NO 20
<211> LENGTH: 15
<212> TYPE: DNA
<213> ORGANISM: Artificial Sequence
<220> FEATURE:
<223> OTHER INFORMATION: Synthetic

<400> SEQUENCE: 20
gatttaaggg aaatg                                                    15

<210> SEQ ID NO 21
<211> LENGTH: 15
<212> TYPE: DNA
<213> ORGANISM: Artificial Sequence
<220> FEATURE:
<223> OTHER INFORMATION: Synthetic

<400> SEQUENCE: 21
catttcccgt caatc                                                    15

<210> SEQ ID NO 22
<211> LENGTH: 15
<212> TYPE: DNA
<213> ORGANISM: Artificial Sequence
<220> FEATURE:
<223> OTHER INFORMATION: Synthetic

<400> SEQUENCE: 22
gattgacggg aaatg                                                    15

<210> SEQ ID NO 23
<211> LENGTH: 15
<212> TYPE: DNA
<213> ORGANISM: Artificial Sequence
<220> FEATURE:
<223> OTHER INFORMATION: Synthetic

<400> SEQUENCE: 23
cagttcacgt aaatc                                                    15

<210> SEQ ID NO 24
<211> LENGTH: 15
<212> TYPE: DNA
<213> ORGANISM: Artificial Sequence
<220> FEATURE:
<223> OTHER INFORMATION: Synthetic

<400> SEQUENCE: 24
gatttacgtg aactg                                                    15

<210> SEQ ID NO 25
<211> LENGTH: 15
<212> TYPE: DNA
<213> ORGANISM: Artificial Sequence
<220> FEATURE:
<223> OTHER INFORMATION: Synthetic

<400> SEQUENCE: 25
```
cagttcccgt caatc                                                    15

<210> SEQ ID NO 26
<211> LENGTH: 15
<212> TYPE: DNA
<213> ORGANISM: Artificial Sequence
<220> FEATURE:
<223> OTHER INFORMATION: Synthetic

<400> SEQUENCE: 26
gattgacggg aactg                                                    15

<210> SEQ ID NO 27
<211> LENGTH: 15
<212> TYPE: DNA
<213> ORGANISM: Artificial Sequence
<220> FEATURE:
<223> OTHER INFORMATION: Synthetic

<400> SEQUENCE: 27
catttcacgt caatc                                                    15

<210> SEQ ID NO 28
<211> LENGTH: 15
<212> TYPE: DNA
<213> ORGANISM: Artificial Sequence
<220> FEATURE:
<223> OTHER INFORMATION: Synthetic

<400> SEQUENCE: 28
gattgacgtg aaatg                                                    15

<210> SEQ ID NO 29
<211> LENGTH: 15
<212> TYPE: DNA
<213> ORGANISM: Artificial Sequence
<220> FEATURE:
<223> OTHER INFORMATION: Synthetic

<400> SEQUENCE: 29
catttccctt caatc                                                    15

<210> SEQ ID NO 30
<211> LENGTH: 15
<212> TYPE: DNA
<213> ORGANISM: Artificial Sequence
<220> FEATURE:
<223> OTHER INFORMATION: Synthetic

<400> SEQUENCE: 30
gattgaaggg aaatg                                                    15

<210> SEQ ID NO 31
<211> LENGTH: 15
<212> TYPE: DNA
<213> ORGANISM: Artificial Sequence
<220> FEATURE:
<223> OTHER INFORMATION: Synthetic

<400> SEQUENCE: 31
cagttcacgt caatc                                                    15

<210> SEQ ID NO 32
<211> LENGTH: 15
<212> TYPE: DNA

```
<213> ORGANISM: Artificial Sequence
<220> FEATURE:
<223> OTHER INFORMATION: Synthetic

<400> SEQUENCE: 32
gattgacgtg aactg                                                   15

<210> SEQ ID NO 33
<211> LENGTH: 15
<212> TYPE: DNA
<213> ORGANISM: Artificial Sequence
<220> FEATURE:
<223> OTHER INFORMATION: Synthetic

<400> SEQUENCE: 33
cagttccctt caatc                                                   15

<210> SEQ ID NO 34
<211> LENGTH: 15
<212> TYPE: DNA
<213> ORGANISM: Artificial Sequence
<220> FEATURE:
<223> OTHER INFORMATION: Synthetic

<400> SEQUENCE: 34
gattgaaggg aactg                                                   15

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
ccttgaaggg atttccctcc                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
ggagggaaat cccttcaagg                                              20

<210> SEQ ID NO 37
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is a, c, g, or t

<400> SEQUENCE: 37 gggrnnyycc                                                         10

<210> SEQ ID NO 38
<211> LENGTH: 21
<212> TYPE: DNA
<213> ORGANISM: Artificial Sequence
<220> FEATURE:
<223> OTHER INFORMATION: Synthetic
```

```
<400> SEQUENCE: 38
ggagggacau cguccaaaat t                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
uuuuggacga ugucccucca c                                              21

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
gggaaattcc gggaaattcc                                                20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
ggaatttccc ggaatttccc                                                20

<210> SEQ ID NO 42
<211> LENGTH: 30
<212> TYPE: DNA
<213> ORGANISM: Artificial Sequence
<220> FEATURE:
<223> OTHER INFORMATION: Synthetic

<400> SEQUENCE: 42
taagagggaa attccgggaa attcctacat                                     30

<210> SEQ ID NO 43
<211> LENGTH: 30
<212> TYPE: DNA
<213> ORGANISM: Artificial Sequence
<220> FEATURE:
<223> OTHER INFORMATION: Synthetic

<400> SEQUENCE: 43
atgtaggaat ttcccggaat ttccctctta                                     30

<210> SEQ ID NO 44
<211> LENGTH: 30
<212> TYPE: DNA
<213> ORGANISM: Artificial Sequence
<220> FEATURE:
<223> OTHER INFORMATION: Synthetic

<400> SEQUENCE: 44
taagagggca attccgggca attcctacat                                     30

<210> SEQ ID NO 45
```

```
<211> LENGTH: 30
<212> TYPE: DNA
<213> ORGANISM: Artificial Sequence
<220> FEATURE:
<223> OTHER INFORMATION: Synthetic

<400> SEQUENCE: 45
taagagggac attccgggac attcctacat                                         30

<210> SEQ ID NO 46
<211> LENGTH: 30
<212> TYPE: DNA
<213> ORGANISM: Artificial Sequence
<220> FEATURE:
<223> OTHER INFORMATION: Synthetic

<400> SEQUENCE: 46
taagagggaa cttccgggaa cttcctacat                                         30

<210> SEQ ID NO 47
<211> LENGTH: 30
<212> TYPE: DNA
<213> ORGANISM: Artificial Sequence
<220> FEATURE:
<223> OTHER INFORMATION: Synthetic

<400> SEQUENCE: 47
atgtaggaat tccccggaat tccctctat                                          30

<210> SEQ ID NO 48
<211> LENGTH: 30
<212> TYPE: DNA
<213> ORGANISM: Artificial Sequence
<220> FEATURE:
<223> OTHER INFORMATION: Synthetic

<400> SEQUENCE: 48
atgtaggaac ttcccggaac ttccctctat                                         30

<210> SEQ ID NO 49
<211> LENGTH: 30
<212> TYPE: DNA
<213> ORGANISM: Artificial Sequence
<220> FEATURE:
<223> OTHER INFORMATION: Synthetic

<400> SEQUENCE: 49
atgtaggact ttcccggact ttccctctta                                         30
```